United States Patent [19]

Hamill et al.

[11] Patent Number: 5,098,834
[45] Date of Patent: Mar. 24, 1992

[54] **PROCESS FOR PRODUCING ANTIBIOTIC A8210 WHICH COMPRISES CULTIVATING *ACTINOMADURA FIBROSA* SP NOV. NRRL 18348, OR AN A82810-PRODUCING MUTANT THEREOF**

[75] Inventors: Robert L. Hamill, Greenwood; Raymond C. Yao, Carmel, both of Ind.

[73] Assignee: Eli Lilly and Company, Indianapolis, Ind.

[21] Appl. No.: 335,332

[22] Filed: Apr. 10, 1989

Related U.S. Application Data

[63] Continuation-in-part of Ser. No. 189,499, May 2, 1988, abandoned.

[51] Int. Cl.$^5$ .......................... C12P 19/44; C12N 1/20
[52] U.S. Cl. ........................................ 435/74; 435/72; 435/825
[58] Field of Search ................. 435/74, 128, 253, 825, 435/72

[56] References Cited

U.S. PATENT DOCUMENTS

| | | | |
|---|---|---|---|
| 4,195,079 | 3/1980 | Celmer et al. | 424/122 |
| 4,407,946 | 10/1983 | Labeda et al. | 435/75 |
| 4,582,822 | 4/1986 | Hamill et al. | 514/25 |
| 4,683,204 | 7/1987 | Boeck | 435/825 |
| 4,746,650 | 5/1988 | Cullen et al. | 514/27 |

FOREIGN PATENT DOCUMENTS

| | | |
|---|---|---|
| 0328303 | 6/1989 | European Pat. Off. . |
| 2090243A | 7/1982 | United Kingdom . |

OTHER PUBLICATIONS

J. tone et al., "CP-47,433 and CP-47,434, New Polycyclic Ether Antibiotics Produced by a New Species of *Actinomadura*", Proc. 11th Intl. Congress of Chemotherapy and 19th ICAAC Meeting, Oct. 1979, pp. 469–470.

G. Nakamura et al., "A New Species of *Actinomadura* Producing a Polyether Antibiotic, Cationomycin", *J. Antibiotics* 36 (11), 1468–1472 (1983).

Meiji Seika Kaisha, Derwent Abstract 87-002439/01 Abstracting Japan Kokai Tokkyo Koho J6 1260-88-8-A, "New Antibiotic SF-2361", Nov. 19, 1986.

Cullen et al., "CP-54,883 A Novel Chlorine-Containing Polyether Antibiotic Produced by a New Species of *Actinomadura*", *J. Antibiotics* 40 (11) 1490–1495 (1987).

Meiji Seika Kaisha, Derwent Abstract No. 87-106351/15 and *Chem. Abstract 107:* 576k of Japan Kokai Tokkyo Koho JP 62 55–090-A (Mar. 10, 1987).

Pfizer, Derwent Abstract 88-030532/05 of European Published Patent EP-255-335-A (Feb. 3, 1988).

Kusakabe et al., "Portmicin, A New Antibiotic", *J. Antibiotics* 40 (2), 237–238 (1987).

*Primary Examiner*—Johnnie R. Brown
*Assistant Examiner*—Elli Peselev
*Attorney, Agent, or Firm*—Steven A. Fontana; Leroy Whitaker; Nancy J. Harrison

[57] ABSTRACT

New Polyether antibiotic A82810, its acyl and alkyl ester, acyl ester and urethane derivatives, and salts thereof, are useful antibacterial and anticoccidial agents and increase feed-utilization efficiency in animals. Methods of making A82810 by culture of *Actinomodura fibrosa* sp. nov. NRRL 18348 and synergistic compositions of the A82810 compounds with nicarbazin, 4,4'-dinitrocarbanilide, certain napthalenamine and benzenamine compounds and metichlorpindol are also provided.

5 Claims, 8 Drawing Sheets

PROCESS FOR PRODUCING ANTIBIOTIC A8210 WHICH COMPRISES CULTIVATING *ACTINOMADURA FIBROSA* SP NOV. NRRL 18348, OR AN A82810-PRODUCING MUTANT THEREOF

CROSS-REFERENCE TO RELATED APPLICATION

This application is a continuation-in-part of Application Serial No. 07/189,499, filed May 2, 1988, now abandoned.

SUMMARY OF THE INVENTION

This invention relates to a new polyether antibiotic, A82810, which is produced by *Actinomadura fibrosa* sp. nov., NRRL 18348. The structure of A82810 is shown in formula 1:

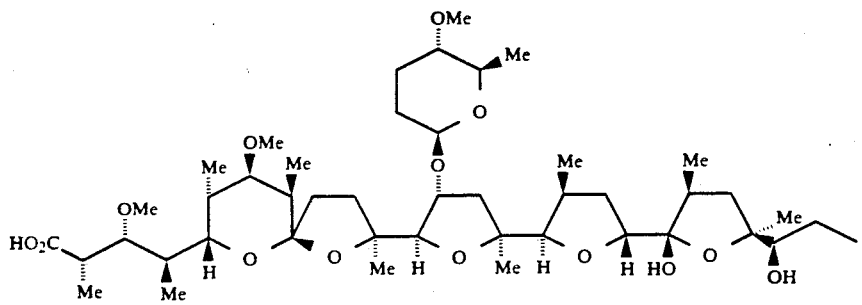

This invention also relates to acyl and alkyl ester and alkyl ether derivatives of A82810 and to the salts of A82810 and of the derivatives.

In addition, this invention provides A82810 urethane derivatives of formula 2:

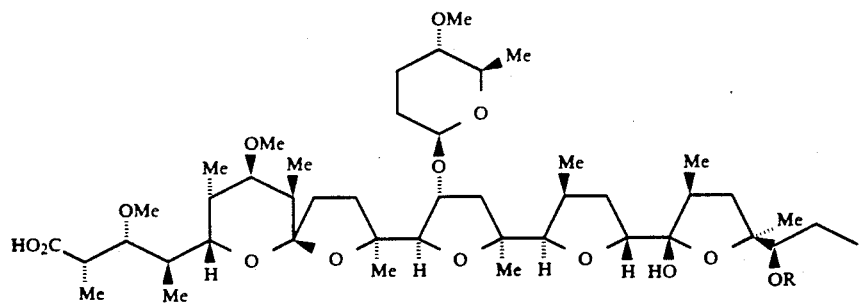

wherein R is —CONHR$_1$ and R$_1$ is alkyl, aryl, alkylaryl, arylalkyl, haloaryl, nitroaryl, haloarylalkyl, alkoxyaryl, aryloxyaryl, arylcycloalkyl, acylaryl and cycloalkyl; and salts of these derivatives.

Another aspect of this invention is the method of producing A82810 by culturing a strain of *Actinomadura fibrosa* sp. nov., NRRL 18348, under submerged aerobic fermentation conditions until a substantial level of the antibiotic is produced. A82810 is extracted from the fermentation broth and from the mycelium with polar organic solvents. A82810 is separated and further purified by techniques such as column raphy.

Because *A. fibrosa* NRRL 18348 is a newly discovered strain, this invention further provides a biologically pure culture of this microorganism.

A82810, its acyl and alkyl ester, alkyl ether and urethane derivatives or a pharmaceutically acceptable salt thereof (an "A82810 compound"), are useful as antibacterial and anticoccidial agents. The compounds S improve feed-utilization efficiency growth performance in both monogastric and ruminant animals. In addition, A82810 has insecticidal and antiviral activity. Methods and compositions pertaining to these uses are part of this invention.

This invention further relates to synergistic compositions of an A82810 compound together with a compound selected from nicarbazin, 4,4'-dinitrocarbanilide, metichlorpindol and certain naphthalenamine or benzenamine compounds. These compositions are useful in controlling coccidiosis in animals. Methods for using these compositions are another aspect of the invention.

DETAILED DESCRIPTION OF THE INVENTION

Animal health products are in great demand. Antibiotics continue to be an important type of animal health product, not only for treating disease, but also for enhancing growth promotion in animals. Antibiotics can promote growth by reducing disease or by increasing feed-utilization efficiency.

One disease which has a serious impact on the poultry industry is coccidiosis. Coccidiosis results from infection by one or more species of Eimeria or Isopora. Improved anticoccidial agents are in demand because of the continuing economic losses due to coccidiosis.

Promoting growth by increasing feed-utilization efficiency is another economically desirable objective of veterinary science. This type of growth promotion is particularly important for ruminants, such as cattle, and for monogastric animals such as poultry and swine.

One group of antibiotics which has been especially important in the animal health field are the polyether antibiotics. For example, the polyether monensin is a valuable commercial product; it is used both for treating coccidiosis in poultry and for increasing feed-utilization efficiency in animals.

A82810 is a new member of the group of polyether antibiotics. Westley (John W. Westley, "Polyether Antibiotics: Naturally Occurring Acid Ionophores, Vol. 2, Chemistry," Marcel Dekker: New York, 1983) has separated existing polyethers by class and type. Using Westley's system, A82810 is a new member of the Class lb, type (1), group of polyethers because it has one spiroketal system. Other members of this group include A80190 (U.S. Pat. No.4,582,822); A-28695 A and B (U.S. Pat. No. 3,839,558); A2041 and II (U.S. Pat. No. 3,705,238); A-32887 (U.S. Pat. No.4,133,876); carriomycin; etheromycin; CP-47,434,RP37454 and the X-14868 antib Characteristics of A82810 Antibiotic A82810 has been assigned structure (based on mass spectrometry and NMR studies). A82810 (in its free acid form) has the following characteristics:

State: white crystals
Mp: 69°–71° C.
pKa: =6 6 (80% aqueous dimethyl sulfoxide)
$[\alpha]^{25}{}_{589}$ D: $-7.35°$ (c 1, MeOH)

Figure 1:
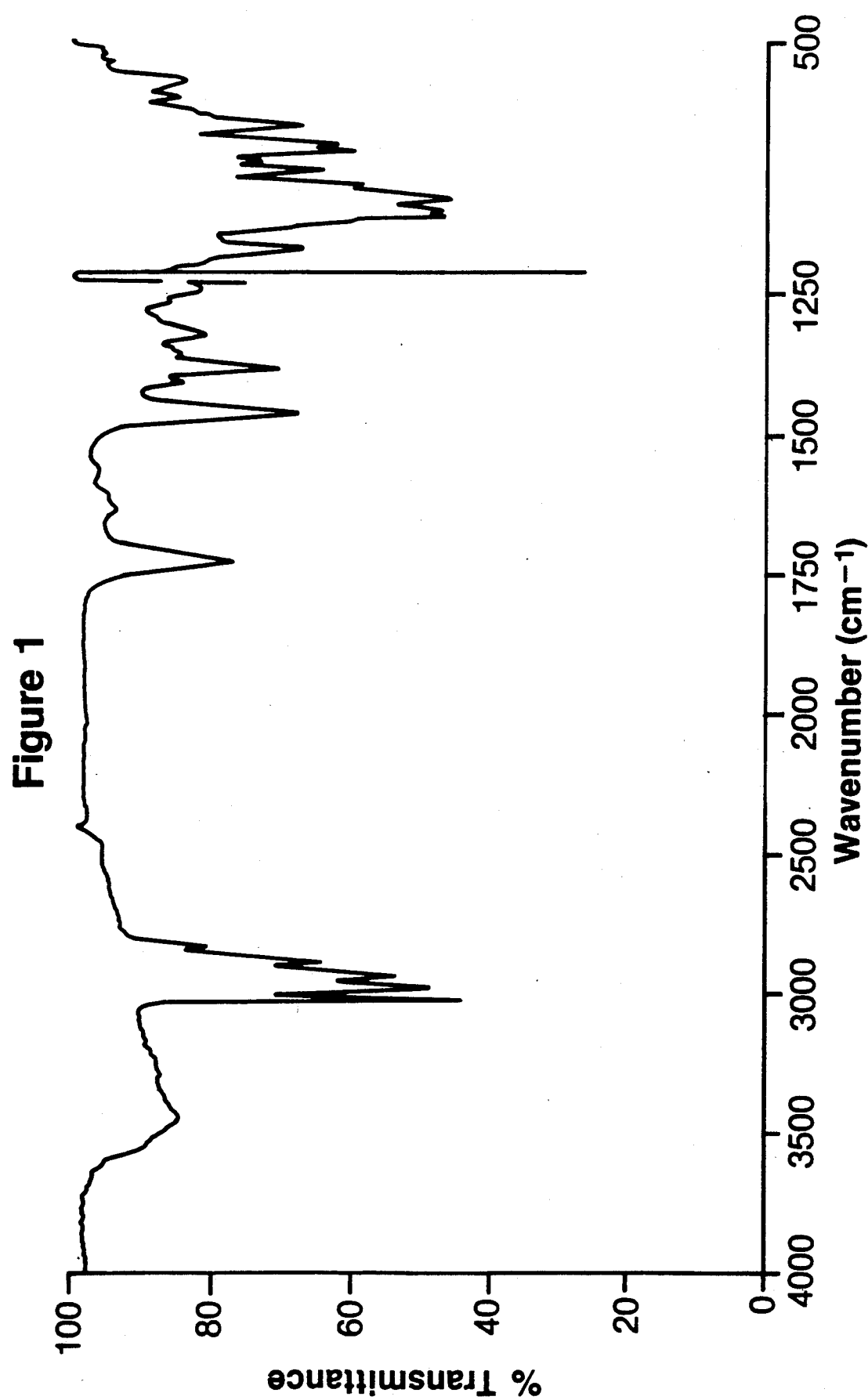
FIG. 1 shows the infrared absorption spectrum of A82810 in chloroform.

Molecular weight: 842 (field desorption mass spectrometry) Empirical formula: $C_{45}H_{78}O_{14}$ UV: end absorbtion only IR (CHCl$_3$): FIG. 1; shows absorption at the following frequencies (cm$^{-1}$) 3020, 2977, 2935, 2880, 1726, 1458, 1379, 1206, 1164, 1146, 1115, 1104, 1094, 1073, 1050, 1025, 1006, 991, 980 and 946

Solubility: Insoluble in water; soluble in lower alcohols such as methanol, ketones such as acetone, esters such as ethyl acetate, halogenated hydrocarbons such as chloroform and hydrocarbons such as diethyl ether, benezene, toluene and warm hexane.

A82810 has an acid function capable of forming salts and ester derivatives and has at least one hydroxyl group which can be esterified or which can form ether derivatives. The acyl and alkyl ester and alkyl ether derivatives of A82810, the urethane derivatives of formula 2, and the pharmaceutically-acceptable salts of A82810 and of these derivatives are also useful as antibiotics and as agents which increase feed-utilization efficiency.

The term "acyl" means a $C_1$ to $C_7$, preferably a $C_1$ to $C_4$, alkanoic acid moiety, i.e., radicals of the formula

wherein $R_{1a}$ is $C_1$ to $C_6$-alkyl or hydrogen, e.g., formyl, acetyl, propionyl, butyryl and the like.

The term "cycloalkyl" means cyclic hydrocarbon groups containing from 3 to 7 carbon atoms, such as, cyclopropyl, cyclobutyl, cyclohexyl and the like, cyclohexyl being preferred. The cycloalkyl group may be substituted by an aryl residue, as defined herein, to form an arylcycloalkyl residue, e.g., 2-(phenyl)cyclopropyl.

The term "alkoxy" means a $C_1$ to $C_7$ lower alkyl group having an oxygen function substituted therein, such as, methoxy, ethoxy, propoxy and the like.

The term "aryl" denotes an aromatic residue derived by the removal of a hydrogen atom from an aromatic hydrocarbon, such as, for example, phenyl, pyridyl or furyl, especially phenyl. The "aryl" residue may be substituted by various groups. A substitutent on a phenyl nucleus is preferably on the 4-position. Examples are 4-alkylaryl, e.q., 4-methylphenyl (4-tolyl); 4-halophenyl, e.g., 4-chlorophenyl; 4-nitrophenyl; 4-aryloxy-aryl, e.g., 4-phenoxyphenyl; 4-alkoxyphenyl, e.g., 4-methoxyphenyl; and 4-(alkyl-carbonyl)phenyl, e.g., 4-(methylcarbonyl)phenyl or 4-(phenylcarbonyl)phenyl.

The term "alkyl" means a $C_1$ to $C_7$ straight or branched chain hydrocarbon, preferably a $C_1$ to $C_4$ hydrocarbon, e.g., methyl, ethyl, propyl, isopropyl, n-butyl, etc. The alkyl group may be substituted by an aryl residue, as defined supra, to form an arylalkyl residue, e.g., phenylethyl or 2-phenylethyl or by a haloaryl residue to form a haloarylalkyl residue, e.g., 4-bromophenethyl.

The salts of A82810 and of its derivatives are useful for separating and purifying the antibiotics. The pharmaceutically-acceptable salts are particularly useful. Examples of salts are the alkali-metal, alkaline-earth-metal and amine salts of A82810 and of its derivatives.

Representative and suitable alkali-metal and alkaline-earth metal salts of A82810 include the sodium, potassium, lithium, cesium, rubidium, barium, calcium and magnesium salts. Suitable amine salts of A82810 include the ammonium and the primary, secondary, and tertiary $C_1$-$C_4$-alkylammonium and hydroxy-$C_2$-$C_4$-alkylammonium salts. Illustrative amine salts inClude those formed by reaction of A82810 with ammonium hydroxide, methylamine, sec-butylamine, isopropylamine, diethylamine, di-isopropylamine, ethanolamine, triethylamine, 3-amino-1-propanol and the like.

When treating an animal, it is not ordinarily of great significance whether the free base or a salt of a compound is used. A salt form may, however, be chosen for reasons of economy, convenience or toxicity.

Antibiotic A82810 is produced by culturing an A82810-producing strain of *Actinomadura fibrosa* sp. nov. under submerged aerobic conditions in a suitable culture medium until substantial antibiotic activity is produced. The antibiotic is recovered using various isolation and purification procedures understood in the art.

The new microorganism of this invention, which produces antibiotic A82810, is called culture A82810 for convenience. Culture A82810 is a natural variant derived from a parent strain (culture A82810) which was isolated from a soil sample from Togo, West Africa.

A culture of the A82810-producing organism has been deposited and made part of the stock culture collection of the Northern Regional Research Center, Agricultural Research, North Central Region, 815

North University Street, Peoria, Illinois, 61604, from which it is available to the public under the accession number NRRL 18348.

Taxonomic studies of the variant were carried out by Frederick P. Mertz of the Lilly Research Laboratories. Based on these studies, the new organism is classified as a new species of the genus *Actinomadura* for which the name *Actinomadura fibrosa* sp. nov. is proposed. This classification is based on laboratory comparison with similar species and comparison of A82810.1's characteristics with published descriptions of the characteristics of similar species.

Methods Used

These studies were made using methods recommended by the International *Streptomyces* Project (ISP) for the characterization of Streptomyces species [E. B. Shirling and D. Gottlieb, "Methods for Characterization of *Streptomyces* Species," *Int. J. Syst. Bacteriol.* 16:313-340 (1966)], as well as methods given by Gordon [R. E. Gordon, D. A. Barnett, J. E. Handerhan, and C. Pang, "*Nocardia coeliaca, Nocardia autotrophica*, and the Nocardin Strain," *Int. J. Syst. Bacteriol.* 24:54-63 (1974)].

Starch hydrolysis was determined by testing for the presence of starch with iodine on ISP No. 4 (inorganic salts-starch agar) plates.

NaCl tolerance was measured by adding NaCl to ISP No. 2 agar to equal the concentration desired.

ICSS-NBS Centroid Color Charts, standard sample No. 2106 (National Bureau of Standards, 1958, U. S. Department of Commerce, Washington, D.C.) and the Color Harmony Manual (4th ed., Container Corporation of America, Chicago, Illinois, 1958) were used to assign color names to the reverse side and to aerial hyphae, respectively.

Morphology was studied using an optical light microscope and a scanning electron microscope (SEM).

The isomers of diaminopimelic acid (DAP) in hydrolysates of whole cells were established by the chromatographic methods of Becker et al. [B. Becker, M. P. Lechevalier, R. E. Gordon, and H. E Lechevalier, "Rapid Differentiation between Nocardia and Streptomyces by Paper Chromatography of Whole-cell Hydrolysates," *Appl. Microbiol.* 12:421-423 (1964)]and of Lechevalier [M. P. Lechevalier, "Identification of - Aerobic Actinomycetes of Clinical Importance," *J. Lab. Clin. Med.* 71:934-944 (1968)].

Resistance to antibiotics was measured by padding antibiotic sensitivity discs onto the surface of seeded ISP No. 2 agar plates. Resistance was scored as (+) when no zone of inhibition was observed and as (−) when a zone of inhibition was observed.

Mycolic acids were determined by a method based on techniques described by Minnikin [D. E. Minnikin, L. Alshamaony and M. Goodfellow, "Differentiation of Mycobacterium, Nocardia, and Related Taxa by Thin-Layer Chromatographic Analysis of Whole-organism Methanolysates," *J. Gen. Microbiol.* 88:200-204 (1975)].

Phospholipids were determined by the procedures of:

(1) M. P. Lechevalier and H. Lechevalier In *A University Laboratory Approach*, Dietz and Thayer (eds.), Special Publication No. 6, Society for Industrial Microbiology, Arlington VA, lg80; pp. 277-284;

(2) D. E. Minnikin, I. G. Hutchinson and A. B. Caldicott, "Thin-layer Chromatography of Methanolysates of Mycolic Acid-containing Bacteria," *J. Chromatography* 188:221-233 (1980); and (3) J. C. Dittmer and R. L. Lester, "A Simple, Specific Spray for the Detection of Phospholipids on Thin-layer Chromatograms, *J. Lipid Research* 5(1):126-128 (1964).

Menaquinone composition was determined by following the procedures of (1) R. M. Kroppenstedt in *Chemical Methods in Bacterial Systematics*, M. Goodfellow and D. E. Minnikin (eds.), 1985, pp. 173-196; and (2) M. D. Collins; ibid, pp. 267-285.

Fatty acid analysis was done using the HP S898A Microbial Identification System (See L. Miller and T. Berger, "Bacterial Identification by Gas Chromatography of Whole Cell Fatty Acids", Hewlett-Packard Application Note 228-41, 1985; 8 pp. Fatty acid methyl esters were made from lyophilized whole cells grown under identical conditions.

Figure 7:
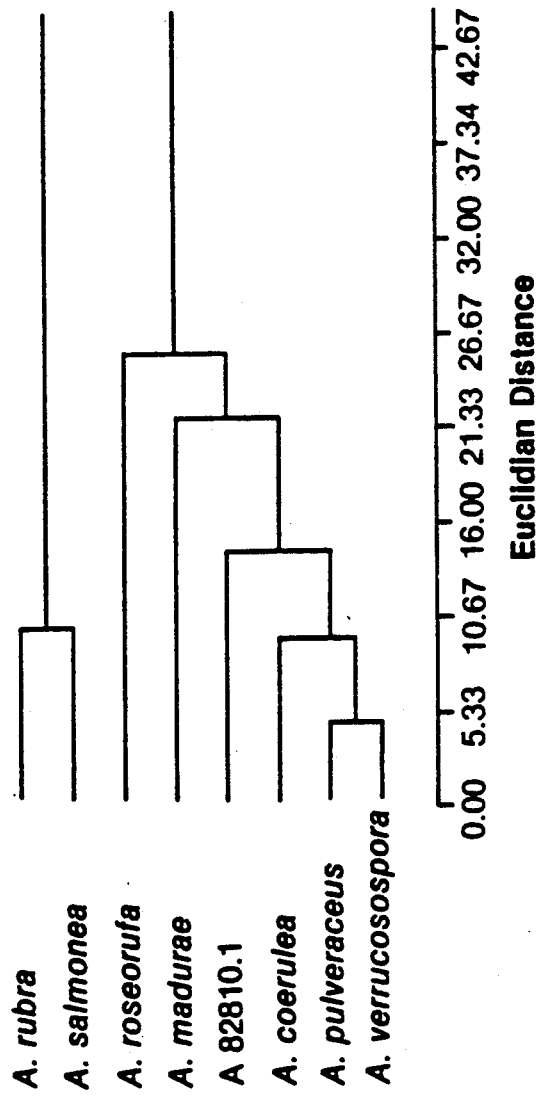
FIG. 7 is a dendrogram comparing *Actinomadura fibrosa* sp. nov. NRRL 18348 (culture A82810.1) with several known Actinomadura species.

The dendrogram shown in FIG. 7 is based on Euclidian distance and was computer generated.

Figure 8:
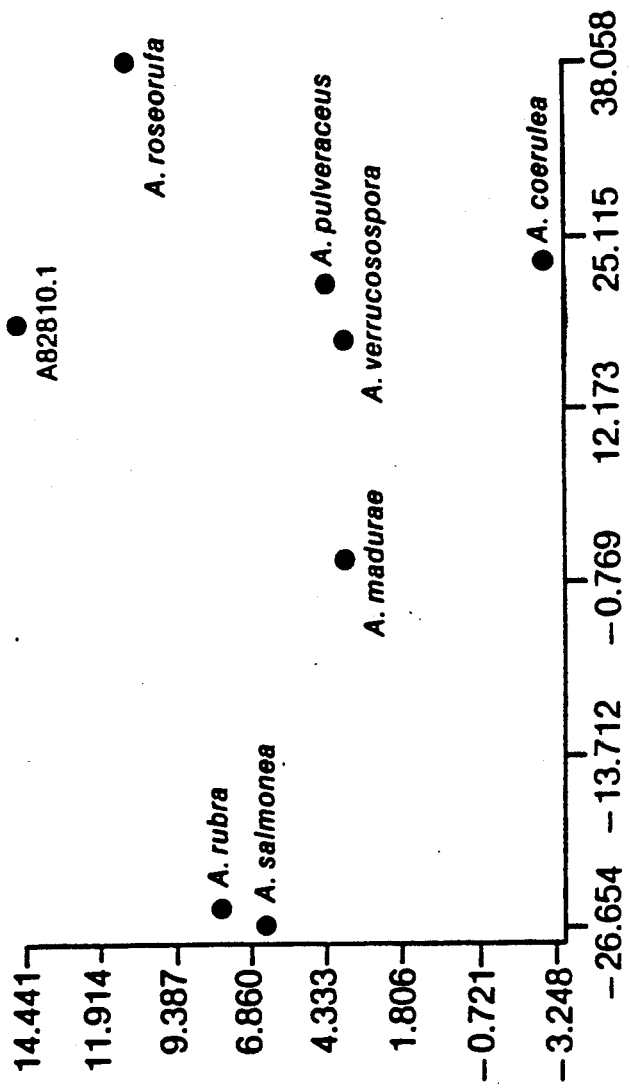
FIG. 8 is a principle component analysis comparing culture A82810.1 with several known Actinomadura species.

The principle component analysis shown in FIG. 8 is two dimensional and was also computer generated.

Cultural Characteristics

Culture A82810.1 grew well on both complex and defined media. However, aerial mycelia were rarely produced except on ISP medium 2, Bennetts agar, and tomato-paste/oatmeal (TPO) agar. When produced, the aerial spore mass was pink to white in color. The reverse side was reddish brown to a distinctive reddish orange color. No soluble pigments were observed. The cultural characteristics of culture A82810are summarized in Table I.

TABLE I

| Cultural Characteristics of A82810.1 on Various Agar Media[a] | |
|---|---|
| Agar Media | A82810.1 Characteristics[b] |
| ISP No. 2 | G: Abundant |
| | R: 55.s.Br |
| | Am: Abundant: b White |
| | Sp: Light brown |
| ISP No. 3 | G: Good |
| | R: 39.gy.rO |
| | Am: Trace:Pink |
| | Sp: None |
| ISP No. 4 | G: Abundant |
| | R: 43.m.rBr. |
| | Am: Trace:Pink |
| | Sp: None |
| ISP No. 5 | G: Abundant |
| | R: 37.m.rO |
| | Am: None |
| | Sp: None |
| ISP No. 7 | G: Abundant |
| | R: 43.m.rBr. |
| | Am: None |
| | Sp: None |
| ATCC No. 172 | G: Good |
| | R: 39.gy.rO |
| | Am: Trace:5ca l.y. Pink |
| | Sp: None |
| Bennett's | G: Abundant |
| | R: 42.l.rBr. |
| | Am: Good:White |
| | Sp: None |
| Emerson | G: Abundant |
| | R: 54.brO |
| | Am: Trace:White |
| | Sp: None |
| Glucose Asparagine | G: Abundant |
| | R: 39.gy.rO |
| | Am: Trace:5ca l.y. Pink |
| | Sp: None |
| Jensens | G: Fair |

TABLE I-continued

Cultural Characteristics of
A82810.1 on Various Agar Media[a]

| Agar Media | A82810.1 Characteristics[b] |
|---|---|
| Nutrient | R: 39.gy.rO |
| | Am: Trace:White |
| | Sp: None |
| | G: Good |
| Potato | R: 53.m.O |
| | Am: None |
| | Sp: None |
| | G: Good |
| Carrot | R: 39.gy.rO |
| | Am: Trace:White |
| | Sp: None |
| TPO | G: Abundant |
| | R: 58.m.Br. |
| | Am: Good:5cb gy.y. Pink |
| | Sp: None |
| Czapek's | G: Good |
| | R: 43.m.rBr |
| | Am: Fair:White |
| | Sp: None |

[a]When incubated at 30° C. for 14 days
[b]G = growth; R = reverse; Am = aerial mycelium; Sp = soluble pigment

Morphological Characteristics

Culture A82810 produced an extensive substrate mycelium. The aerial hyphae were unusual. S When observed under light microscopy and SEM, segmentation into spores was not observed. The hyphae appeared to be completely asporogenous. Numerous bundles of hyphae forming thick fibers were readily apparent. Some of these aerial hyphae formed short knobs or projections which bore some resemblance to spores. Examination with SEM indicated that these structures were not true spores. Occasionally, other fibrous structures were observed. These structures, in addition to the fibrous appearance of the aerial hyphae in general, were the basis for the species name fibrosa.

Physiological Characteristics

Culture A82810 produced acid from the following carbohydrates: adonitol, L-arabinose, cellobiose, fructose, galactose, glucose, glycerol, glycogen, lactose, maltose, mannose, rhamnose, ribose, sucrose, trehalose and xylose. A82810 did not produce acid from: D-arabinose, cellulose, dextrin, dulcitol, ethanol, erythritol, inositol, inulin, mannitol, melizitose, melibiose, alpha-methyl-D-glucoside, raffinose, salicin, sorbitol, sorbose, and xylitol.

Culture A82810.1 utilized the following organic acids (as sodium salts): acetate, butyrate, propionate and pyruvate. It did not utilize benzoate, citrate, formate, lactate, malate, mucate, oxalate, succinate and tartrate.

A82810.1 decomposed casein, elastin, esculin, hypoxanthine, starch, testosterone, tyrosine and urea, but did not decompose adenine, allantoin, calcium malate, guanine, hippurate and xanthine.

A82810.1 produced catalase, phosphatase and urease; liquified gelatin; hydrolyzed skim milk and was able to survive at 50° C. for 8 hours. It did not produce melanoid pigments or $H_2S$, reduce nitrates or peptonize skim milk.

A82810.1 was resistant to cephalothin (30 μg), lincomycin (2 μg), penicillin G (10 units), rifampin (5 μg) and lysozyme (50 μg/mL). It was sensitive to bacitracin (10 units), gentamicin (10 μg), neomycin (30 μg), oleandomycin (15 μg), streptomycin (10 μg), tetracycline (30 μg), tobramycin (10 μg) and vancomycin (30 μg).

Culture A82810.1 grew in a temperature range of 20°–45° C. An optimum growth temperature appeared to be 37° C. The culture tolerated NaCl at levels up to and including 5%.

Cell-Wall Analysis

Hydrolyzed whole cells contain meso-diaminopimelic acid. The following sugars were detected in the whole cell extracts: galactose, glucose, mannose, madurose and ribose. Thus, A82810.1 has a type III cell wall and a type B sugar pattern [See M. P. Lechevalier and H. Lechevalier, "Chemical Composition as a Criterion in the Classification of Aerobic Actinomycetes", Int. J. Syst. Bacteriol. 20:435–443 (1970)].

Mycolic acids were not detected.

Phospholipid determinations on the whole cell indicated the presence of phosphatidyl inositol, diphosphatidyl glycerol and GluNu (an unknown structure containing glucosamine). Neither phosphatidyl ethanolamine nor phosphatidyl choline was detected. Therefore, A82810.1 has a type IV phospholipid pattern [See M. P. Lechevalier, A. E. Stern, and H. A. Lechevalier, "Phospholipids in the Taxonomy of Actinomycetes," Actinomycetes, K. P. Schaal and G. Pulverer (eds); Zbl. Bakt. Suppl. 11, Gustav Fischer Verlag, Stuttgart, New York, 1981].

The menaquinones detected in A82810.1 were hexahydrogenated menaquinones with nine isoprene units, MK-9($H_6$) and a minor amount of octahydrogenated I menaquinones, MK-9($H_8$).

Identity of Strain A82810.1

The chemotaxonomic properties and the cultural and morphological characteristics of A82810.1 support the assignment of the isolate to the genus Actinomadura (See V. B. D. Skerman, V. McGowan, and P.H.A. Sneath, *Approved Lists of Bacterial Names,* American Society for Microbiology, Washington D.C., 1980).

Twenty three type strains of Actinomadura species were grown along with culture A82810.1 on 21 different agar media. Cultural and morphological characteristics were compared. Culture A82810.1 showed a similarity to the following *A. coerulea, A. madurae, A. pulveraeeus, A. roseorufa, A. rubra, A. salmonea* and *A. verrucosospora.*

Biochemical characteristics of these seven species were gathered from the literature and compared with A82810.1 by constructing a table of similarity coefficients. The coefficient of Jaccard SJ, and the simple matching coefficien $S_{sm}$ were used (W. Kurylowicz, A. Paszkiewicz, W. Woznicka, W. Kurzatkowski and T. Szulga, *Numerical Taxonomy of Streptomycetes,* Polish Medical Publishers, Warsaw, 1975, p. 37).

Table II summarizes this data.

TABLE II

Comparison of A82810.1 with several
Actinomadura Species using Similarity Coefficients[a]

| Culture | Sj | $S_{sm}$ |
|---|---|---|
| A82810.1 | 100 | 100 |
| A. verrucosospora | 72 | 81 |
| A. madurae | 73 | 79 |
| A. salmonea | 70 | 78 |
| A. rubra | 70 | 76 |
| A. roseorufa | 60 | 75 |

TABLE II-continued

Comparison of A82810.1 with several
Actinomadura Species using Similarity Coefficients[a]

| Culture | Sj | S$_{sm}$ |
|---|---|---|
| A. pulveraceus | 59 | 74 |

[a]Data for A. coerulea was unavailable.

Fatty acid analyses were performed on the whole cells of these cultures. A dendrogram and a principle component analysis obtained from this data are shown in FIGS. 7 and 8, respectively.

The similarity coefficients and the fatty acid analyses indicate that, of the seven known species compared, A82810.1 shares the most characteristics with *A pulveraceus* and *A. verrucosospora*. However, the similarities are insufficient to conclude that A82810.1 is a strain of either species. Table III shows the differences between A82810.1 and these two species.

TABLE III

Differences Between A82810.1, *A. pulveraceus* and *A. verrucosospora*

| Characteristic | A82810.1 | A. pulveraceus | A. verrucosospora |
|---|---|---|---|
| Urease production | + | − | − |
| Guanine hydrolysis | − | ND[a] | + |
| Starch hydrolysis | + | + | − |
| Acid production from: | | | |
| L-arabinose | + | − | + |
| Dextrin | − | ND | + |
| Fructose | + | − | + |
| Inositol | − | + | − |
| Lactose | + | − | + |
| Mannitol | − | − | + |
| Mannose | + | − | − |
| Trehalose | + | − | + |
| Utilizes Sodium Acetate | + | − | ND |
| Growth at 45° C. | + | − | − |
| Presence of spores | − | + | + |
| Bluish gray spore color | − | + | − |
| Resistance to: | | | |
| Oleandomycin (16 μg) | − | ND | + |
| Penicillin G (10 units) | + | ND | − |
| Tolerates 5% NaCl | + | ND | − |

[a]ND = not done

This study supports the conclusion, therefore, that culture A82810.1 is a new species of Actinomadura. For this reason, culture A82810.1 has been named *Actinomadura fibrosa* sp. nov., the latin adjective S fibrosa referring to the fibrous appearance of the aerial hyphae.

As is the case with other organisms, the characteristics of the A82810 -producing culture of this invention, *Actinomadura fibrosa* sp. nov. NRRL 18348, are subject to variation. Mutants of the strain may be obtained by methods known in the art, for example, by treatment with various physical and chemical mutagens such as ultraviolet light, X rays, gamma rays and chemicals such as n-methyl-N'-nitro-N-nitrosoguanidine. Natural and induced mutants of *Actinomadura fibrosa* sp. nov. NRRL 18348 which retain the characteristic of A82810 production are considered part of this invention.

The culture medium used to grow the *Actinomadura fibrosa* culture can be any one of a number of media. For economy in production, optimal yield, and ease of product isolation, however, certain culture media are preferred. Thus, for example, preferred carbohydrate sources in large-scale fermentation are glucose and potato dextrin, although ribose, xylose, fructose, galactose, mannose, mannitol, and the like can also be used.

Preferred nitrogen sources are enzyme-hydrolyzed casein and yeast, although liver meal, meat peptones, fish meal, and the like are also useful. Among the nutrient inorganic salts which can be incorporated in the culture media are the customary soluble salts capable of yielding zinc, sodium, magnesium, calcium, ammonium, chloride, carbonate, sulfate, nitrate and like ions.

Essential trace elements necessary for the growth and development of the organism should also be included in the culture medium. Such trace elements commonly occur as impurities in other substituents of the medium in amounts sufficient to meet the growth requirements of the organism. Foaming is not usually a problem, but small amounts (i.e. 0.2 mL/L) of an anti-foam agent such as polypropylene glycol may be added to large scale fermentation media if needed.

For production of substantial quantities of antibiotic A82810, submerged aerobic fermentation in tanks is preferred. Small quantities of A82810 may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The vegetative inoculum medium can be the same as that used for larger fermentations, but other media are also suitable.

A82810 is produced by the A82810-producing organism when grown at temperatures between about 25° and about 40° C. An optimum temperature for A82810 production appears to be about 34°–36° C.

As is customary in submerged aerobic culture processes, sterile air is blown into the vessel from the bottom while the medium is stirred with conventional turbine impellors. The maximum oxygen uptake of the fermentation under the conditions used thus far has not exceeded about 0.35 mM/L/minute. In a fully baffled 165-liter fermentor containing approximately 115 liters of broth, an aeration rate of 0.125 v/v/m with an agitation rate of 300 rpm is sufficient to maintain the level of dissolved oxygen at or above 45% of air saturation at a pressure of 0.34 atmospheres.

Production of antibiotic A82810 can be followed during the fermentation by testing samples of the broth for antibiotic activity against organisms known to be sensitive to the antibiotic. One assay organism useful in testing A82810 is *Bacillus subtilis* ATCC 6633. The bioassay is conveniently performed by the agar-well diffusion test.

Following its production under submerged aerobic fermentation conditions, A82810 can be recovered from the fermentation medium by methods used in the fermentation art. The antibiotic activity produced during fermentation of the A82810-producing organism occurs both in the filtered broth and in the mycelial mass. Maximum recovery of A82810 is accomplished, however, by initially filtering the medium to separate the broth from the mycelial mass. The filtered broth and the mycelial mass can then be purified separately to give their respective portion of A82810. A variety of techniques may be used in this purification. A preferred technique for purification of the filtered broth involves adjusting it to a pH of about 9 and extracting with a suitable solvent such as, for example, ethyl acetate. The extracting solvent can then be evaporated under vacuum to give the broth portion of A82810.

A preferred method of purifying the mycelial mass is to extract the separated mycelial filter cake with a suitable solvent such as, for example, acetone. The extracting solvent is then evaporated under vacuum to give a concentrated aqueous solution. This aqueous solution is then adjusted to a pH of about 9 and is extracted with a suitable solvent such as, for example, ethyl acetate. The extracting solvent is then concentrated under vacuum to give the mycelial portion of A82810.

The broth and mycelial portions of A82810 are further purified by similar procedures. A preferred procedure involves silica gel chromatography.

Alternatively, the culture solids, including medium constituents and mycelium can be used without extraction or separation, but preferably after removal of water, as a source of A82810. For example, after production of A82810, the whole fermentation broth can be dried by lyophilization, by drum-drying, or by azeotropic distillation and drying. The dried broth is then mixed directly into feed premix.

The alkali-metal and alkaline-earth-metal cationic salts of A82810 are prepared according to procedures commonly used for the preparation of cationic salts. For example, the free acid of A82810 is dissolved in a suitable solvent such as acetone; a ½ volume of water is added; and this solution is adjusted to a pH of about 9 to 10 with the base of the desired cationic salt (e.g. NaOH, KOH). The salt thus formed can be isolated by routine methods, such as filtration or evaporation of the solvent.

A preferred method of forming salts is to dissolve A82810 (acid form) in a water-immiscible solvent such as ethyl acetate, add an equal volume of water, and adjust the mixture to pH 10 with the corresponding cationic base (e.g. NaOH, KOH, etc.) The separated organic phase is washed with water and concentrated to dryness. The residue is lyophilized from dioxane. The salt can be crystallized from an appropriate solvent, such as hexane.

The salts formed with organic amines can be prepared similarly. For example, the gaseous or liquid amine can be added to a solution of A82810 in a suitable solvent such as acetone; the solvent and excess amine can be removed by evaporation.

A82810 acyl-ester derivatives are prepared by treating A82810 with a corresponding acid anhydride or acid chloride. Esterification occurs at one of the A82810 hydroxyl groups. Such esters are typically prepared by reacting A82810 with, for example, the corresponding acid anhydride at room temperature.

A82810 alkyl ester derivatives are prepared by esterification of the carboxyl group, using standard procedures. The A82810 alkyl ester derivatives are typically less active when tested in vitro. When administered to an animal, however, such esters can act as pro drugs which are converted to A82810 in vivo.

The alkyl ether derivatives of A82810 are those compounds wherein one or more of the hydroxyl groups has been replaced by a $YR_2$ group wherein:

Y represents 0 or S; and $R_2$ represents $C_1-C_6$-alkyl, $C_1-C_4$-alkoxy-$C_2-C_5$-alkyl, $C_1-C_4$-alkoxycarbonyl-$C_2-C_5$-alkyl, amino-$C_2-C_5$alkyl mercapto-$C_2-C_5$-alkyl, hydroxyalkyl, haloalkyl, or $(R')_m$-phenyl$(CH_2)_n$-,
wherein $R'$ represents $C_1-C_4$-alkyl, $C_1-C_4$-alkoxy, or hydroxy;

m represents 0-2; and n represents 0-3.

The terms alkyl and alkoxy have the meaning discussed supra, but are limited to the number of carbon atoms specified.

The term "hydroxyalkyl" refers either to a hydroxy-$C_2-C_5$-alkyl moiety or, when Y is 0, to the 2,3-dihydroxyprop-l-yl moiety.

The term "haloalkyl" refers to a $C_2-C_5$-alkyl moiety having from one to three halogen substituents, selected from the group consisting of bromine, chlorine, and fluorine. When the alkyl moiety is dihalo- or trihalo-substituted, the halo-substituents must be the same halogen moiety.

Preferred A82810 ether derivatives are those compounds wherein Y represents 0 and R represents $C_1-C_6$-alkyl. The ether derivatives are prepared by reacting A82810, or a salt thereof, with a corresponding primary alcohol or thiol.

With some of the starting alcohols or thiols it may be necessary to add an acid catalyst to the reaction. Suitable catalysts include hydrochloric acid, sulfuric acid, methanesulfonic acid, benzenesulfonic acid, toluenesulfonic acid, selenium dioxide, and boron trifluoride.

A solvent such as, for example, water, acetone, benzene, ether, tetrahydrofuran, or dioxane may be added to facilitate the reaction. Reactions generally occur at room temperature, although higher temperatures may be used.

Although ordinary reaction work-up procedures are sometimes sufficient, additional purification may be required to obtain the compounds of this invention. Such purification may be accomplished by well-known methods, such as, for example, column chromatography, thin-layer chromatography, fractional crystallization and the like.

The A82810 urethane derivatives of formula 2 can be prepared by treating A82810 or an A82810 salt with an isocyanate of formula 3

$$R_1-NCO \qquad (3)$$

wherein $R_1$ is as defined supra.

Preferably, a salt of A82810, in particular the sodium salt, is used. The isocyanate of formula 3 should be added in slight excess, e.g., about 10% excess, in order to form the mono derivative in optimum quantity. The reaction is preferably carried out in an inert solvent such as a chlorinated hydrocarbon, e.g., carbon tetrachloride, methylene chloride or chloroform, ether, ethyl acetate or in an aromatic hydrocarbon solvent such as benzene or toluene. The reaction temperature is not critical but can be between above 0° C. and the boiling point of the reaction mixture, but is preferably about room temperature.

The A82810 compounds have antibacterial and anticoccidial activity. A82810 compounds are especially active against anaerobic bacteria. The minimal inhibitory concentrations (MIC's) at which A82810 inhibits various bacteria, as determined by standard agar-dilution assays, are summarized in Tables IV and V. End points were read after 24-hour incubation.

TABLE IV

In Vitro Antibacterial Activity of Antibiotic A82810

| Test Organism | MIC (mcg/mL) |
|---|---|
| Staphylococcus aureus X1.1 | 1.0 |
| Staphylococcus aureus V41 | 1.0 |
| Staphylococcus aureus X400 | 1.0 |
| Staphylococcus aureus S13E | 1.0 |
| Staphylococcus epidermidis 270 | 1.0 |
| Staphylococcus epidermidis 222 | 0.5 |
| Streptococcus pyogenes C203 | 1.0 |
| Streptococcus pneumoniae Park 1 | 1.0 |
| Streptococcus faecium X66 | 1.0 |
| Streptococcus faecalis 2041 | 1.0 |
| Haemophilus influenzae C.L. | 128 |
| Haemophilus influenzae 76 | 64 |
| Escherichia coli N10 | 1.0 |
| Escherichia coli EC14 | 8.0 |
| Escherichia coli TEM | >128 |
| Enterobacter aerogenes C32 | 8.0 |
| Enterobacter aerogenes EB17 | 8.0 |
| Klebsiella sp. | >128 |
| Salmonella sp. | >128 |
| Pseudomonas aeruginosa X528 | 2.0 |
| Pseudomonas aeruginosa X239 | 0.25 |
| Pseudomonas aeruginosa PS18 | >128 |
| Pseudomonas aeruginosa PS72 | 0.25 |
| Serratia marcescens X99 | >128 |
| Proteus sp. | >128 |
| Shigella sonnei | 2.0 |

TABLE V

Susceptibility of Anaerobic Bacterial Isolates to Antibiotic A82810

| Anaerobic Bacteria | MIC (mcg/mL) |
|---|---|
| Clostridium difficile 2994 | 0.5 |
| Clostridium perfringens 81 | 0.5 |
| Clostridium septicum 1128 | 0.5 |
| Eubacterium aerofaciens 1235 | ≦0.25 |
| Peptococcus asaccharolyticus 1302 | ≦0.25 |
| Peptococcus prevoti 1281 | ≦0.25 |
| Peptostreptococcus anaerobius 1451 | ≦0.25 |
| Peptostreptococcus intermedius 1624 | ≦0.25 |
| Propionibacterium acnes 79 | 2 |
| Bacteroides fragilis 111 | 8 |
| Bacteroides fragilis 1877 | 8 |
| Bacteroides fragilis 1936B | 8 |
| Bacteroides thetaiotaomicron 1438 | 8 |
| Bacteroides melaninogenicus 1856/28 | 8 |
| Bacteroides melaninogenicus 2736 | 8 |
| Bacteroides vulgatis 1211 | 4 |
| Bacteroides corrodens 1874 | 8 |
| Fusobacterium symbiosum 1470 | 0.5 |
| Fusobacterium necrophorum 6054A | ≦0.25 |

Anticoccidial activity is an important property of the A82810 compounds. For example, in an in vitro tissue-culture screen against *Eimeria tenella*, A82810 was active at <0.0025 mcg/mL, propionyl-A82810 was active at 0.05 mcg/mL and acetyl-A82810 was active at 0.01 mcg/mL.

For treating coccidiosis in poultry, a non-toxic anticoccidial amount of an A82810 compound is administered to infected or susceptible birds, preferably orally on a daily basis. The A82810 compound can be supplied in many ways, but it is most conveniently supplied with a pharmaceutically acceptable carrier, preferably the feed ingested by the birds. Although a variety of factors must be considered in determining an appropriate concentration of A82810 compound, the rates of administration are generally in the range of about 0.5 to about 100 ppm in the feed and are preferably in the range of about 1 to about 25 ppm of feed ration.

In another aspect, this invention relates to compositions for treating coccidiosis. One group of compositions are those comprising an effective amount of an A82810 compound for treating coccidiosis, together with a suitable vehicle.

Previously, a number of compounds were found to have a synergistic effect on the anticoccidial activity of one or more polyether antibiotics. For example, anticoccidial combinations comprising nicarbazin or 4,4'-dinitrocarbanilide and polyether antibiotics were disclosed by Maurice E. Callender and Thomas K. Jeffers in U.S. Pat. No. 4,218,438. Albert J. Clinton and George O. P. O'Doherty found that certain napthalenamines and benzenamines had a synergistic effect on the anticoccidial activity of some polyether antibiotics [See U.S. Pat. Nos. 4,764,534 and 4,366,168, respectively]. A coccidiocidal combination of monensin and metichlorpindol was disclosed by Larry R. McDougald in U.S. Pat/ No.4,061,755.

Nicarbazin and 4,4'-dinitrocarbanilide are described in U.S. Patent 2,731,382. Nicarbazin is a complex of 4,4'-dinitrocarbanilide and 2-hydroxy-4,6-dimethylpyrimidine, dimethylpyrimidine, but the 4,4'-dinitrocarbanilide alone exhibits anticoccidial activity [See *Science* 122, 244 (1955)].

The A82810 compounds of this invention also exhibit synergistic effects with these types of compounds. Thus, another group of compositions of this invention are compositions for controlling coccidiosis in poultry comprising: (1)
  (a) an A82810 compound of formula 1:
  (b) an A82810 urethane derivative of formula 2 or
  (c) a pharmaceutically acceptable salt of an (a) or (b) compound;
in combination with
  (2)
  a compound selected from the group consisting of
  (a) nicarbazin,
  (b) 4,4'-dinitrocarbanilide,
  (c) a napthalenamine compound of formula 4:

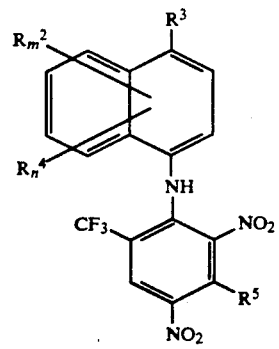

wherein:
$R^2$ is $C_1$–$C_4$ alkyl;
$R^3$ is halogen, $C_1$–$C_4$ fluoroalkyl, $C_1$–$C_4$ fluoroalkoxy or $C_1$–$C_4$ fluoroalkylthio;
$R^4$ is halogen;
$R^5$ is hydrogen or halogen;
m is 0, 1 or 2; and
n is 0 or 1;
with the proviso that, when an $R^4$ substituent exists, it is at other than the 2-position;
(d) a benzenamine selected from 2,4-dinitroN-[4-(trifluoromethoxy)phenyl]-6-(trifluoromethyl)benzenamine; 2,4-di phenyl]-6-(trifluoromethyl)benzenamine or 2,4-dinitro-(pentafluoroethoxy)phenyl]-6-(trifluoromethyl)benzenamine;

(e) metichlorpindol: or (f) a pharmaceutically acceptable salt of an (a)–(e) compound.

In formula 4, $C_1$–$C_4$ alkyl includes methyl, ethyl, n-propyl, isopropyl, n-butyl, sec.-butyl, isobutyl, t-butyl, and the like.

The term "halogen" represents fluorine, chlorine, bromine and iodine.

$C_1$–$C_4$ Fluoroalkyl is a $C_1$–$C_4$ alkyl group bearing one or more fluorine atoms. Such fluoroalkyl groups include trifluoromethyl, 1,1,2,2-tetrafluoroethyl, pentafluoroethyl, 1,2,3,3-tetrafluoropropyl, nonafluorobutyl, and the like.

$C_1$–$C_4$ Fluoroalkoxy is a $C_1$–$C_4$ alkoxy group one or more fluorine atoms. Such fluoroalkoxy groups include difluoromethoxy, trifluoromethoxy, 1-fluoroethoxy, 1,1,2,2-tetrafluoroethoxy, pentafluoroethoxy, 1,2,2,3,3-pentafluoropropoxy, heptafluoropropoxy, 4,4,4-trifluorobutoxy, and the $C_1$–$C_4$ Fluoroalkylthio is a $C_1$–$C_4$ alkylthio group bearing one or more fluorine atoms. Such fluoroalkylthio groups include trifluoromethylthio, 1,1,2,2-tetrafluoroethylthio, pentafluoroethylthio, 4,4,4-trifluorobutylthio, and the like. Preferred formula 4 compounds are those wherein m and n are 0 and $R^5$ is hydrogen.

Typical formula 4 compounds are:

4-Fluoro-N-[2,6-dinitro-6-(trifluoromethyl)-phenyl]-1-naphthalenamine

4-Iodo-N-[2,6-dinitro-6-(trifluoromethyl)-S phenyl]-1-naphthalenamine

4-Trifluoromethyl-N-[2,6-dinitro-6-(trifluoromethyl)-phenyl]-1-naphthalenamine

4-Pentafluoroethyl-N-[2,6-dinitro-6-(trifluoromethyl)-phenyl-1-naphthalenamine 6,7-Dimethyl-4-(1,1,2,2-tetrafluoroethoxy)-N--dinitro-6-(trifluoromethyl)phenyl]-l-naphthalenamine 2-Isopropyl-4-chloro-N-[3-chloro-2,4-dinitro-6-(trifluoromethyl)phenyl]-l-naphthalenamine 8-n-Butyl-4-(4,4,4-trifluorobutoxy)-N-[3-bromo-2,4-dinitro-6-(trifluoromethyl)phenyl]-l-naphthalenamine 3-Methyl-6-propyl-4-heptafluoropropyl-N-[2,4-dinitro-6-(trifluoromethyl)phenyl]-l-naphthalenamine 3,4-Dichloro-N-[2,4-dinitro-6-(trifluoromethyl)phenyl]-1-naphthalenamine 4-(1,1-Difluoroethoxy)-N-[2,4-dinitro-6-(trifluoromethyl)phenyl]-1-naphthalenamine 4-(1,1,2,2-Tetrafluoroethoxy)-N-[2,4-dinitro-6-(trifluoromethyl)phenyl]-l-naphthalenamine and 4-(1,1,2,2-Tetrafluoroethylthio)-N-[2,4-dinitro-6-(trifluoromethyl)phenyl]-l-naphthalenamine.

The components of the combinations of an A82810 compound with compounds 2(a)–(e) are used in amounts which, in combination, are synergistic as to at least one coccidiosis-causing organism. In general, the maximum amounts to be used in the Combinations are the same as the maximum amounts for anticoceidial treatment by the individual components. The lower limits are generally less than that required for therapy by the individual components. Accordingly, the present invention is generally practiced with compositions containing 1) from about 0.5 to about 100 ppm of an A82810 compound and 2) a) from about 5 to 125 ppm of nicarbazin, b) from about 25 to about 150 ppm of 4,4'-dinitrocarbanilide, c) from about 1 to about 1000 ppm of the specified naphthalenamine, d) from about 1 to about 125 ppm of a specified benzenamine, or e) from about 20 to about 70 ppm of metichlorpindol. The A82810 compounds are particularly effective when administered with a benzeneamine, naphthaleneamine or nicarbazin. Preferred combinations contain from about 2 to about 20 ppm of an A82810 compound with from about S to about 80 ppm of a benzeneamine, naphthaleneamine or nicarbazin.

Another important property of the A82810 compounds is the ability to improve feed-utilization efficiency in animals. For example, the A82810 compounds improve feed-utilization efficiency in ruminants which have a developed rumen function. The efficiency of feed use can be monitored by observing the production and concentration of propionate compounds in the rumen using the method described by Arthur P. Raun in U.S. Pat. No. 3,794,732 (see especially Example 5). The A82810 compounds are typically effective in increasing propionates and, thereby, the efficiency of feed utilization, when administered to ruminants orally at rates of from about 0.02 mg/kg/day to about 1.5 mg/kg/day. Preferable rates of administration are from about 0.05 mg/kg/day to about 0.5 mg/kg/day.

A preferred method of administration is to mix the compound with the animals' feed; however, it can be administered in other ways, for example, tablets, drenches, boluses, or capsules. Formulation of these various dosage forms can be accomplished by methods well known in the veterinary pharmaceutical art. Each individual dosage unit should contain a quantity of a compound of this invention directly related to the proper daily dose for the animal to be treated.

This invention further relates to feed compositions adapted to increase feed utilization comprising feed ration and from 2 to 40 grams per ton of an A82810 compound.

In another aspect the A82810 compounds are useful in the treatment of swine dysentery. A82810 inhibits the growth of Treponema hyodysenteriae, a causative agent of swine dysentery, at levels as low as 1.56 mcg/mL. A preferred method of administration to swine is by incorporation of an appropriate amount of an A82810 compound into the feed ration or drinking water. An appropriate amount will relate to whether the treatment is to prevent or to cure infection. Usually, a lower concentration of active compound is needed to prevent infection than is required for to eliminate infection in animals already afflicted. In general, amounts in the range of from about 20 to about 100 grams of A82810 compound per ton of feed are effective to prevent infection. Amounts in the range of from about 100 to about 500 g of A82810 compound per ton of feed are recommended for treating swine suffering from dysentery. These amounts provide from about 1 to about 5 mg/kg of body weight per day (prophylactic treatment) or from about 5 to about 25 mg/kg of body weight per day (treatment of infected animal). When added to the drinking water, amounts of from about 0.04 to about 0.2 g (prophylactic) or from about 0.2 to about 1 g (therapeutic) of A82810 compound per gallon of water are recommended.

This invention further relates to feed compositions for treating swine dysentery comprising swine ration and an effective amount of an A82810 compound for this purpose. As discussed, an effective amount is typically one in the range of from about 20 to about 500 grams of A82810 compound per ton of feed.

As described supra, A82810 compounds are active against anaerobic bacteria, including *Clostridium perfringens*. A82810 compounds should, therefore, be beneficial in the treatment or prevention of enteritis in chickens, swine, cattle and sheep. A82810 compounds are also useful in the treatment of enterotoxemia in ruminants.

The A82810 compounds also have antiviral activity. For example, tissue-culture tests show that A82810 is active against Herpes simplex viruses (HSV I and II) at levels as low as 1.56 mcg/mL and Friend leukemia virus at levels as low as 0.04 mcg/mL. In other tissue-culture tests, A82810 was active against Great Lakes and Brazil influenza viruses at a level of 250 mcg/mL.

In addition, the A82810 compounds have some anthelmintic activity. For example, in vitro studies, A82810 (Na salt) inhibited *Caenorhabditis elegans* when administered at a level of 50 ppm (85% inhibition), measured at 72 hr.

The A82810 compounds can be administered to animals orally or parenterally. They can also be administered by insufflation, i.e. by blowing the antibiotic, in the form of a medicated dust, into an enclosed space or room wherein the animals or poultry are held. The animals or poultry breathe the medicated dust present in the air; the medicated dust also is taken into the body through the eyes (a process called intraocular injection).

The most practical way to administer the A82810 compounds is by formulation into the feed supply. A variety of feeds, including the common dry feeds, liquid feeds, and pelleted feeds, may be used. Although the preferred method of administration is by mixing it with the animals' feed, it can also be administered in other ways, for example, tablets, drenches, boluses, or capsules. Each individual dosage unit should contain a quantity of A82810 compound directly related to the proper daily dose for the animal to be treated.

The methods of formulating drugs into animal feeds are well known. A preferred method is to make a concentrated drug premix which in turn is used to prepare medicated feeds. Typical premixes may contain from about 1 to about 200 grams of drug per pound of premix Premixes may be either liquid of solid preparations.

The final formulation of feeds for animals or poultry will depend upon the amount of drug to be administered. The common methods of formulating, mixing, an pelleting feeds may be used to prepare feeds containing an A82810 compound.

The A82810 compounds may be formulated for parenteral administration by methods recognized in the veterinary pharmaceutical art. Effective injectable compositions containing the A82810 compounds may be in either suspension or solution form. In the solution form, the A82810 compound is dissolved in a physiologically acceptable carrier. Such carriers comprise a suitable solvent, preservatives such as benzyl alcohol, if needed, and buffers. Useful solvents include, for example, alcohols, glycols, or inert oils such as vegetable oils or highly refined mineral oils.

Injectable suspension compositions are prepared using a nonsolvent for the compound with adjuvants, as a carrier. The nonsolvent can be, for example, water or a glycol such as polyethylene glycol.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful for suspending the compounds. Lecithin, alkylphenol polyethylene oxide adducts, naphthalenesulfonates, alkylbenzenesulfonates, and the polyoxyethylene sorbitan esters are useful suspending agents in liquid nonsolvents.

Many substances which affect the hydrophilicity, density, and surface tension of the liquid nonsolvent can assist in making injectable suspensions in individual cases. For example, silicone antifoams, glycols, sorbitol, and sugars can be useful suspending agents.

In the preparation of dusts or powders for administration by insufflation, the compounds are typically mixed with talc, diatomaceous earth, or some other inert substance as an adjuvant.

The A82810 compounds are also useful as insecticides. For example, A82810 is active against southern armyworm, spider mite and blowfly larvae at levels as low as 100 ppm and against adult stablefly at levels as low as 50 ppm.

In order to illustrate more fully the operation of this invention, the following examples are provided:

EXAMPLE 1

Preparation of A82810

A. Shake-flask Fermentation of A82810

Use the culture *Actinomadura fibrosa* sp. nov. NRRL 18348, either as a lyophilized pellet or as a suspension maintained in liquid nitrogen, to inoculate a seed medium having the following composition:

| Seed Medium I | |
|---|---|
| Ingredient | Amount (%) |
| Glucose | 1.0 |
| Soluble starch | 2.0 |
| Yeast extract | 0.5 |
| Enzymatic hydrolysate of casein* | 0.5 |
| CaCO$_3$ | 0.1 |
| Deionized water | q.s. 1 liter |
| Unadjusted pH = 6.6; add NaOH to raise the pH to 7.2 before sterilizing; post-sterilization pH = 6.8. | |

*NZ Amine A, Sheffield Chemical Co., Norwich, N.Y.

Prepare slants or plates by adding 2% agar to the seed medium. Incubate the inoculated slant at 30° C. for from about 10 to about 14 days. Scrape the mature slant culture with a sterile tool to loosen the spores and remove and mascerate the mycelial mat. Use about one-fourth of the loosened spores and culture growth to inoculate 50 mL of a first-stage seed medium.

Incubate the inoculated first-stage medium in a 250-mL Erlenmeyer flask at 30° C. for about 120 hours on a shaker orbiting in a two-inch (5.08 cm) circle at Use this incubated first-stage medium (0.4 mL) to inoculate 50 mL of a production medium having the following composition:

| Production Medium I | |
|---|---|
| Ingredient | Amount (/L) |
| Glucose | 5.0 g |
| Enzymatic hydrolysate of casein* | 3.0 g |
| Yeast extract | 5.0 g |
| Blackstrap molasses | 15.0 g |
| MgSO$_4$ (anhydrous) | 1.0 g |
| CaCO$_3$ | 2.0 g |

-continued

| Production Medium I | |
|---|---|
| Ingredient | Amount (/L) |
| Potato dextrin | 25.0 g |
| Methyl oleate | 20.0 mL |
| Cold tap water | q.s. 1 liter |
| (Adjust presterilization pH to 7.0 with 5N NaOH) | |

*NZ Amine A

Incubate the inoculated production medium in a 250-mL wide-mouth Erlenmeyer flask at 30°-32° C. for to 10 days on a shaker orbiting in a two-inch circle at 250 rpm.

B. Tank Fermentation of A82810

In order to provide a larger volume of inoculum, use 10 mL of incubated first-stage medium, prepared as described in Section A, to inoculate 400 mL of a second-stage growth medium having the same composition as that of the first-stage medium. Incubate this second-stage vegetative medium in a 2-L wide-mouth Erlenmeyer flask for about 72 hours at 30° C. on a shaker orbiting in a two-inch circle at 250 rpm.

Use this incubated second-stage vegetative medium (800 mL) to inoculate 115 L of sterile production medium (prepare as described in Section A except add antifoam agents). Allow the inoculated production medium to ferment in a 165-L stirred fermentation tank for 8 to 10 days at a temperature of 34° C. Maintain a dissolved oxygen level above 40% of air saturation with low airflow (0.12–0.25 v/v/m) and low rpm (150–200) in the stirred vessel.

EXAMPLE 2

A82810 is produced using the method of Example 1, except that in Section B: 1) the second-stage vegetative medium has the following composition:

| Second-Stage Medium II | |
|---|---|
| Ingredient | Amount (g/L) |
| Yeast extract | 5.0 |
| Glucose | 5.0 |
| Potato dextrin | 10.0 |
| MgSO$_4$.7H$_2$O | 2.0 |
| Glycerol | 1.0 |
| Deionized water | q.s. to 1 liter |
| Unadjusted pH = 6.5; no pH adjustment; post-sterilization pH = 6.4. | | and 2) the production medium has the following composition:

| Production Medium II | |
|---|---|
| Ingredient | Amount (g/L) |
| Glucose | 10.0 |
| Pork liver meal | 15.0 |
| Blackstrap molasses | 5.0 |
| MgSO$_4$.7H$_2$O | 0.5 |
| Potato dextrin | 25.0 |
| Tap water | q.s. to 1 liter |
| Unadjusted pH = 6.1; adjust to 7.0 with about 170 mL of 5N NaOH; post-sterilization pH = 6.4. | |
| Antifoam added: Sag 471 (0.2 g/L) and P-2000 (0.1 mL/L). | |

EXAMPLE 3

A82810 is produced using the procedures of Example 1, except that: (1) the seed medium is:

| Seed Medium II | |
|---|---|
| Ingredient | Amount (g/L) |
| Trypticase soy broth | 30 |
| Yeast extract | 3 |
| Glucose | 5 |
| Maltose | 4 |
| MgSO$_4$.7H$_2$O | 2 |
| Deionized water | |
| pH is 7.0 without adjustment | |

(2) the inoculated first-stage medium is incubated at 36° C. for 48 hr; 3) the inoculated second-stage medium is incubated at 36° C. for 24 hr; and 4) the production medium volume is 10 L, incubation temperature is 36° C., and composition is:

| Production Medium III | |
|---|---|
| Ingredient | Amount (g/L) |
| Potato dextrin | 30 |
| Glucose | 10 |
| Enzymatic hydrolysate of casein* | 3 |
| Yeast | 5 |
| Blackstrap molasses | 15 |
| MgSO$_4$ (anhydrous) | 1 |
| CaCO$_3$ | 2 |
| Tap Water | q.s. to 1 liter |
| Unadjusted pH = 6.3; adjust to pH 7.0 with 5N NaOH; post-sterilizaton pH = 6.4. | |
| Antifoam added: Sag 471 (0.2 g/L) and P-2000 (0.5 mL/L). | |

*NZ Amine A

EXAMPLE 4

Isolation of A82810

Whole fermentation broths from two 100-L tanks, prepared in a manner similar to that described in Examples 1 and 2, were combined (215 L) and filtered through a filter press, using a filter aid (3%, Hyflo Super-Cel, Manville Products Corp., Lompoc CA 93436) to yield 180 L of filtrate.

The mycelial filter cake was extracted twice with acetone (60 L each). The acetone extracts were combined and concentrated in vacuo to a volume of about 18 L. The concentrate was combined with the broth filtrate. This mixture was adjusted to pH 9 with 5N sodium hydroxide, and the resulting solution was extracted with ⅔ volume of ethyl acetate, mixing for 1 hr and chilling overnight. The ethyl acetate extract (115 L) was separated, mixed with a small amount of filter aid and filtered. The clarified extract was concentrated in vacuo to a residue.

This residue was dissolved in toluene (200 mL), and the solution was applied to a column containing 2 L of silica gel (Grace Grade, 20–300 mesh) packed in toluene. The column was washed with toluene (10 L) and developed with toluene:ethanol [sequentially with 10 L each of (98:2), (96:4) and (90:10)], collecting 1-L fractions.

Elution of A82810 was monitored by bioassay using *Bacillus subtilis* and lysis of red-blood-cell agar plates. Fractions containing most of the A82810 (#13–20) were combined and concentrated to an oil. This oil was dissolved in dioxane (200 mL) and freeze-dried to yield crude A82810, also as an oil.

The crude A82810 was dissolved in chloroform (200 mL) and applied to a column containing 2 L of silica gel (Grace Grade 62, 20-300 mesh), packed in chloroform. The column was washed with chloroform (10 mL) and developed with chloroform acetone [sequentially with 10 L each of (9:1), (4:1), (7:3) and (1:1)]and then with acetone (10 L), collecting 1-L fractions.

Fractions were monitored by bioassay and were pooled according to bioassay results as follows: #6-9 (pool A), #10-18 (pool B) and #19-28 (pool C). Each pool was concentrated to a residue which was dissolved in dioxane and freeze-dried. Pools A and C yielded oils and had to be further purified, whereas pool B yielded 9.9 g of A82810 as a white powder.

Pool A was dissolved in acetone (900 mL) and added to water (1 L). The pH of the solution was adjusted to 9.0 with 5N NaOH, and the solution was concentrated in vacuo to a volume of about 1 L. The concentrate was extracted twice with toluene, and the combined extracts were concentrated and freeze-dried from dioxane to yield an additional 2.8 g of A82810 as a white powder.

Pool C was treated in the same manner but was still an oil after freeze-drying. The oil was dissolved in acetonitrile (50 mL), whereupon crystals formed immediately. The crystals were filtered and dried in vacuo to yield another 1244 mg of pure A82810 as the sodium salt (mp 173°-175° C.).

EXAMPLE 5

Crystallization of A82810 Sodium Salt

Amorphous A82810 sodium salt (400 mg) was suspended in hexane (50 mL) by sonification in a test tube and then allowed to stand at room temperature. The crystals which formed on the side of the tube were removed and dried in vacuo to yield 50 mg of pure A82810 sodium salt (mp 255°-257° C.).

Figure 2:
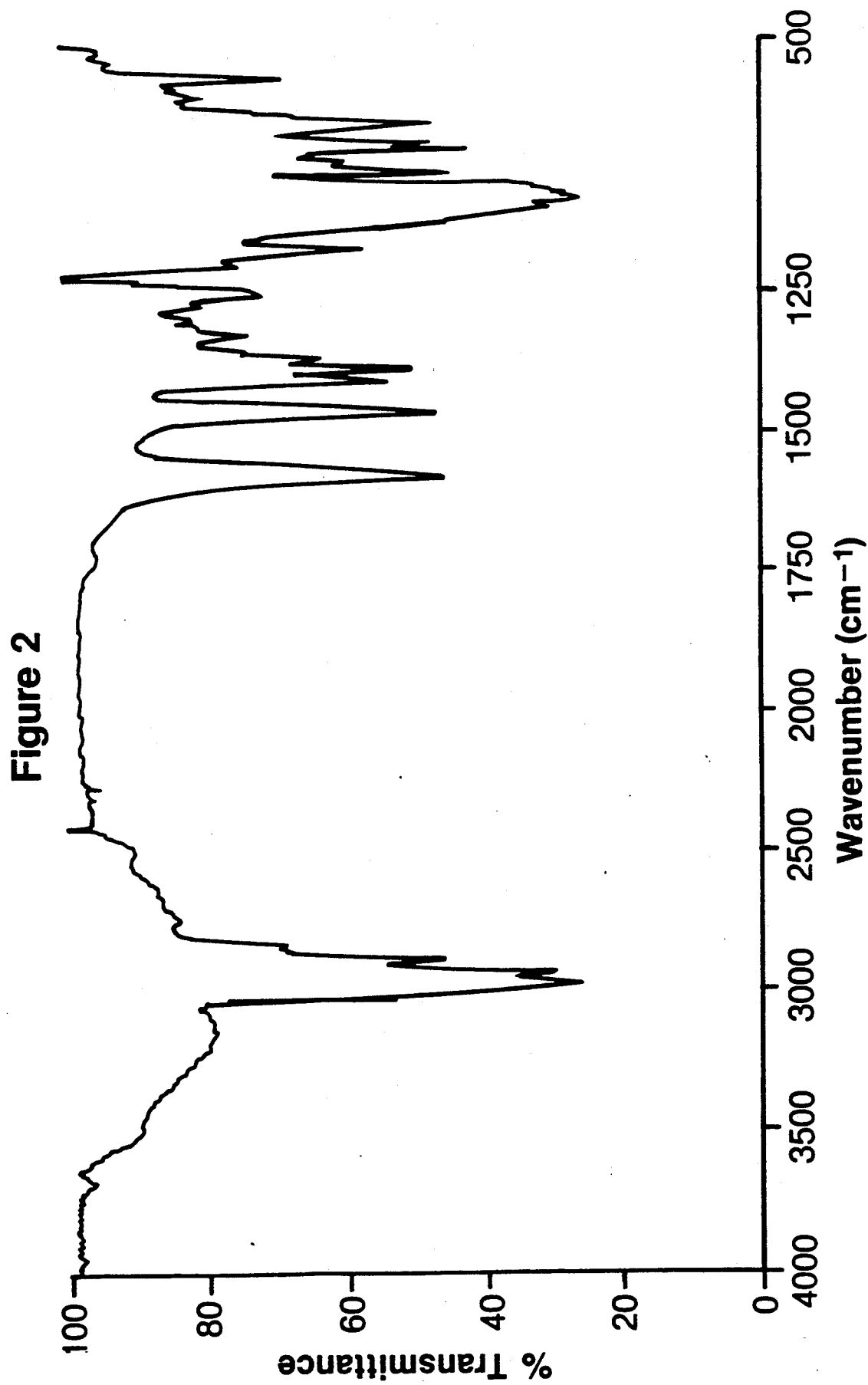
FIG. 2 shows the infrared absorption spectrum of A82810 sodium salt in chloroform.

IR in $CHCl_3$, shown in FIG. 2, shows absorption maxima at the following frequencies ($cm^{-1}$): 3020, 2970, 2952, 2936, 2679, 1570, 1458, 1393, 1380, 1363, 1359, 1163, 1115, 1093, 1075, 1067, 1054, 1027, 1010, 1001, 990, 979 and 940.

EXAMPLE 6

Preparation of A82810

(free acid)

A82810 (Na salt, 200 mg), obtained as described in Example 4, is dissolved in dioxane (75 mL). Water (25 mL) is added to this solution; the pH of the resulting solution is adjusted to pH 3 by the addition of 1 N HCl. The acidified solution is stirred for one hour and then is extracted twice with chloroform (100 mL each). The chloroform extracts are combined and concentrated under vacuum to give A82810 free acid.

EXAMPLE 7

Preparation of Acetyl-A82810

A82810 (sodium salt, 200 mg) was dissolved in pyridine (4 mL); acetic anhydride (4 mL) was added; and the mixture was allowed to stand for 40 hours at room temperature. Water (10 mL) was added, and the aqueous solution was extracted with chloroform (50 mL). The chloroform extract was washed successively with 50 mL each of 0.1 N HCl, water containing 1 percent $NaHCO_3$, and water. The chloroform extract was then concentrated in vacuo to a residue, and the residue was dissolved in acetone. The acetone solution was concentrated in vacuo to remove residual pyridine and acetic acid. This step was repeated three times, and the resulting residue was dissolved in benzene and freeze-dried to yield 204 mg of acetyl-A82810 (Na salt).

Molecular weight =906 by fast-atom bombardment mass spectrometry (FABMS).

Figure 3:
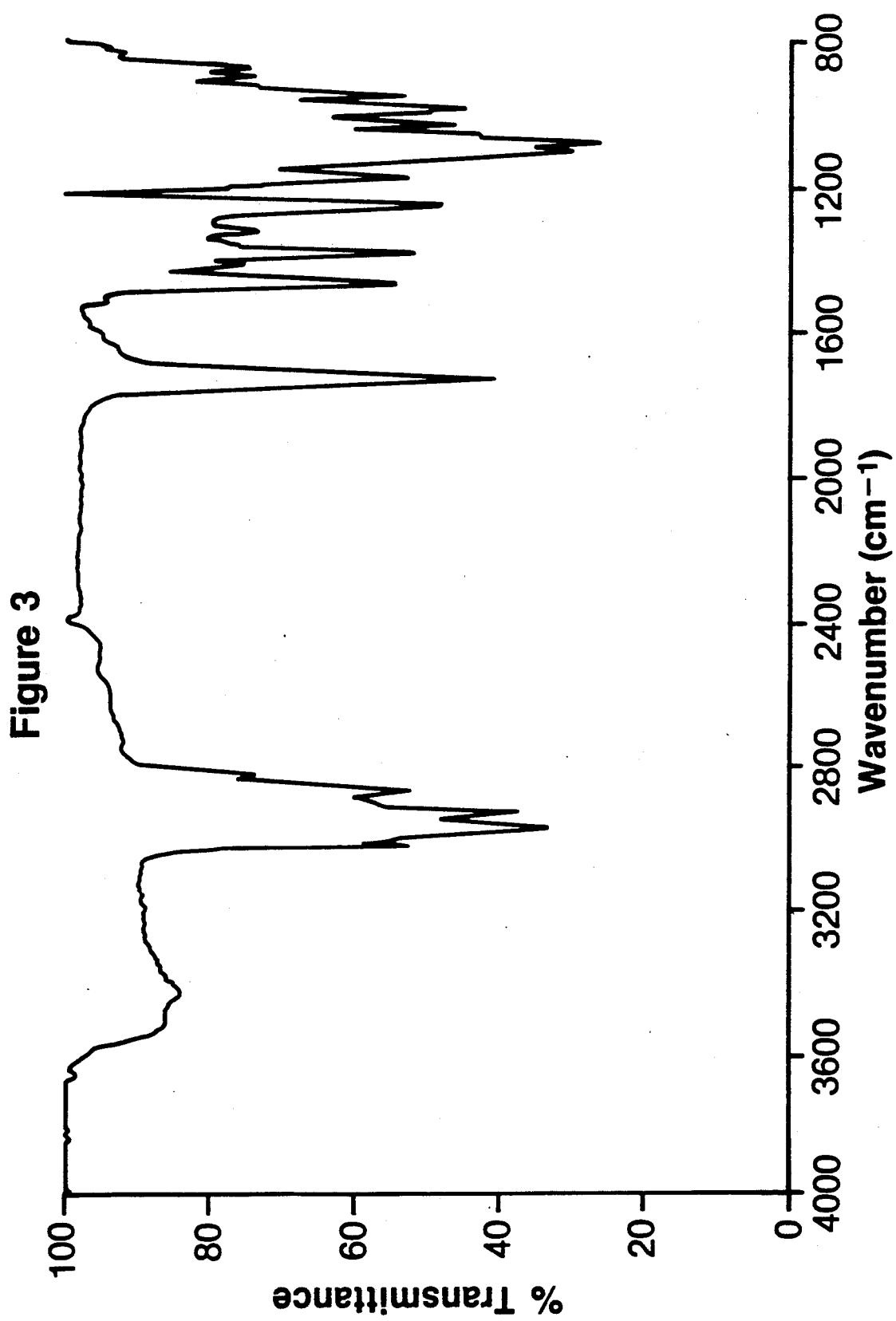
FIG. 3 shows the IR spectrum of A82810 acetyl ester derivative in chloroform.

IR in $CHCl_3$, shown in FIG. 3, shows absorption maxima at the following frequencies ($cm^{-1}$) 3021, 2976, 2935, 2880, 2831, 1728, 1458, 1379, 1357, 1321, 1314, 1247, 1226, 1223, 1201, 1185, 1101, 1094, 1076, 1056, 1024, 990, 981, 947, 929, 896 and 875.

EXAMPLE 8

Preparation of Propionyl-A82810

A82810 (sodium salt, 200 mg) was dissolved in pyridine (4 mL); propionic anhydride (4 mL) was added; and the mixture was allowed to stand at room temperature for 44 hours. Water (10 mL) was added, and the solution was extracted with chloroform (50 mL). The chloroform extract was washed successively with 50 mL each of 0.1N HCl, water containing 1 percent $NaHCO_3$ and water. The chloroform extract was concentrated in vacuo to a residue which was dissolved in acetone (100 mL). The acetone solution was concentrated in vacuo to remove residual pyridine and propionic acid. This step was repeated three times. The residue was dissolved in benzene and freeze-dried to yield propionyl A82810 (Na salt) as an oil.

The oil was dissolved in acetonitrile (5 mL) and applied to a column containing 20 mL of silica gel (Woelm, 100-200 $\mu$m) packed in acetonitrile. The washed with acetonitrile (100 mL) and developed with acetonitrile:acetone [successively with mL each of (9:1), (4:1), (7:3) and (1:1)]and finally with acetone (100 mL), collecting 25-mL fractions.

Elution was monitored by silica-gel thin-layer chromatography, developing with acetonitrile:acetone (1:1) and detecting with vanillin-$H_2SO_4$ spray. Fractions containing the majority of the propionyl A82810 (sodium salt #13-23) were combined and concentrated in vacuo to give a residue. The residue was dissolved in dioxane and freeze-dried to yield 47 mg of the desired ester.

Molecular weight =920 by FDMS.

Figure 4:
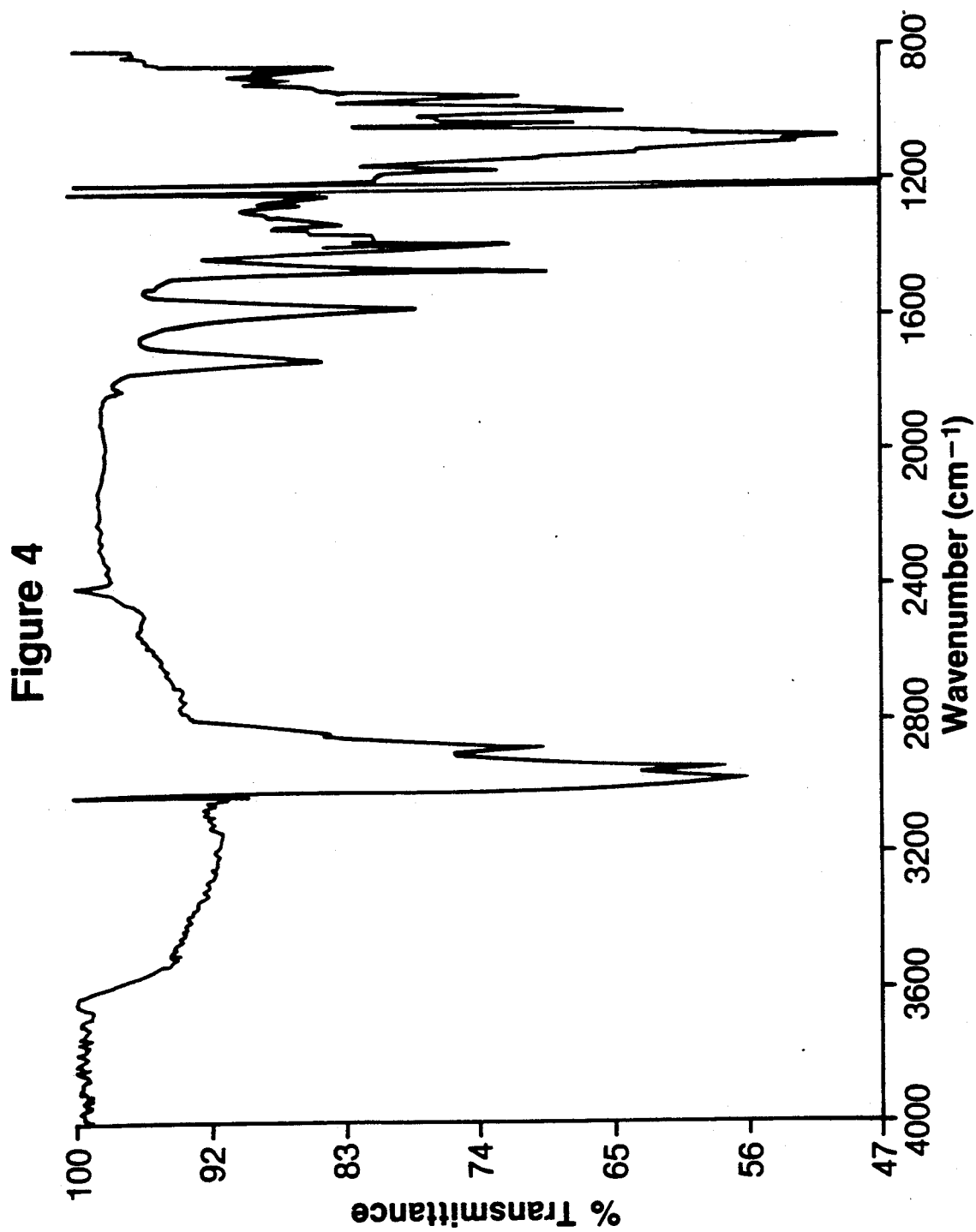
FIG. 4 shows the IR spectrum of A82810 propionyl ester derivative in chloroform.

IR in $CHCl_3$, shown in FIG 4, shows absorption maxima at the following frequencies ($cm^{-1}$): 2975, 2971, 2935, 2879, 2831, 1571, 1457, 1398, 1380, 1364, 1359, 1321, 1237, 1225, 1216, 1213, 1191, 1163, 1116, 1093, 1076, 1068, 1054, 1027, 1010, 1001, 990, 980, 945, 940, 929 and 861.

EXAMPLES 9-11

The following A82810 ester derivatives can be prepared using the method of Examples 7-8:
n-Heptanoyl-A82810
Valeryl-A82810
tert-Butyryl-A82810

EXAMPLE 12

Preparation of A82810 4-Bromophenylurethane Derivative

A82810 (sodium salt, 200 mg) was dissolved in benzene (25 mL), and 4-bromophenyl isocyanate (225 mg) in benzene (25 mL) was added with stirring. One drop of triethylamine was added, and the mixture was stirred at room temperature for 160 hours. The precipitate which formed was separated by filtration, and the filtrate was freeze-dried to give 400 mg of the A82810 4-bromophenylurethane derivative (sodium salt).

Molecular weight =1061 by FDMS.

Figure 5:
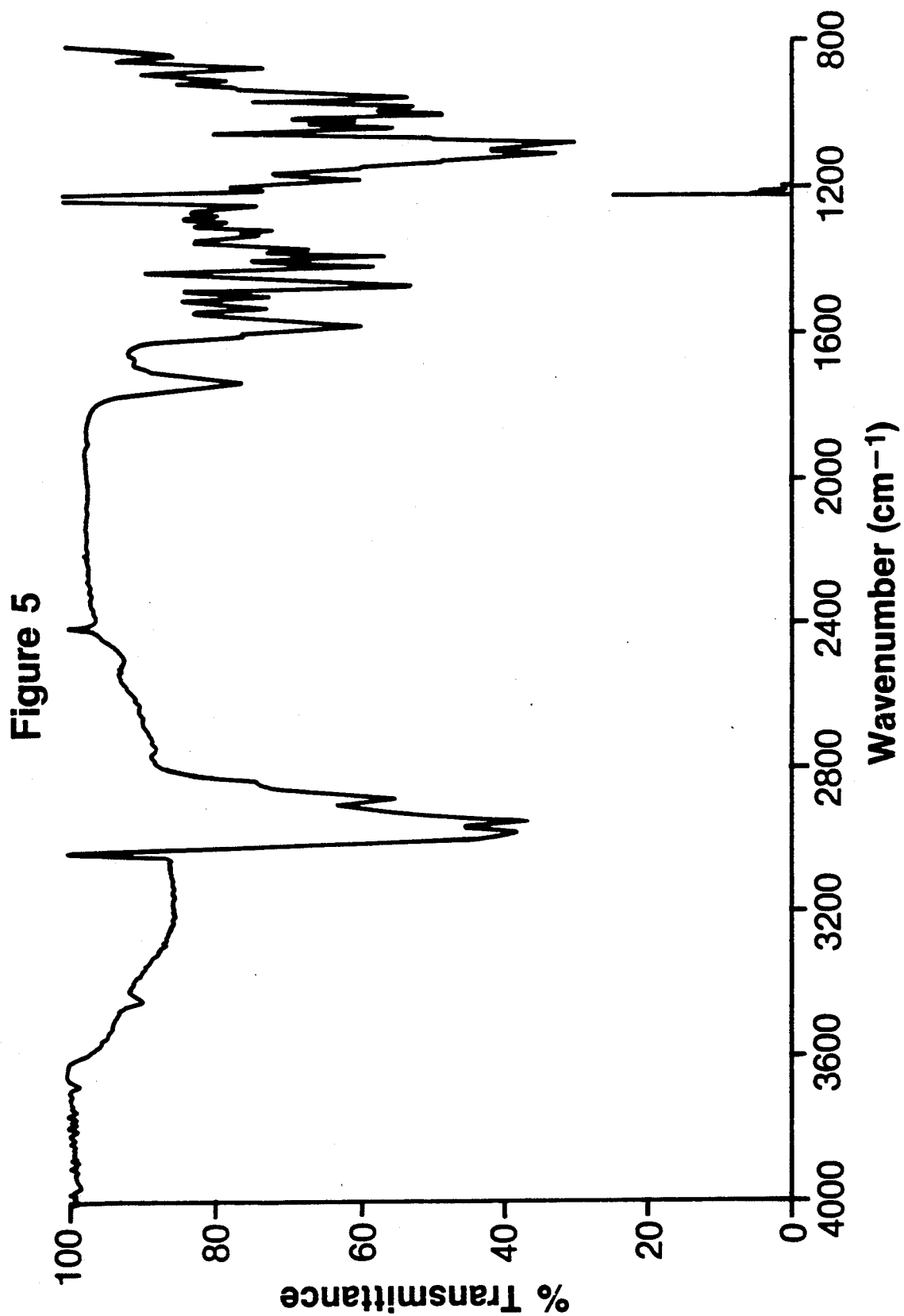
FIG. 5 shows the infrared absorption spectrum of A82810 4-bromophenylurethane derivative in chloroform.
Figure 6:
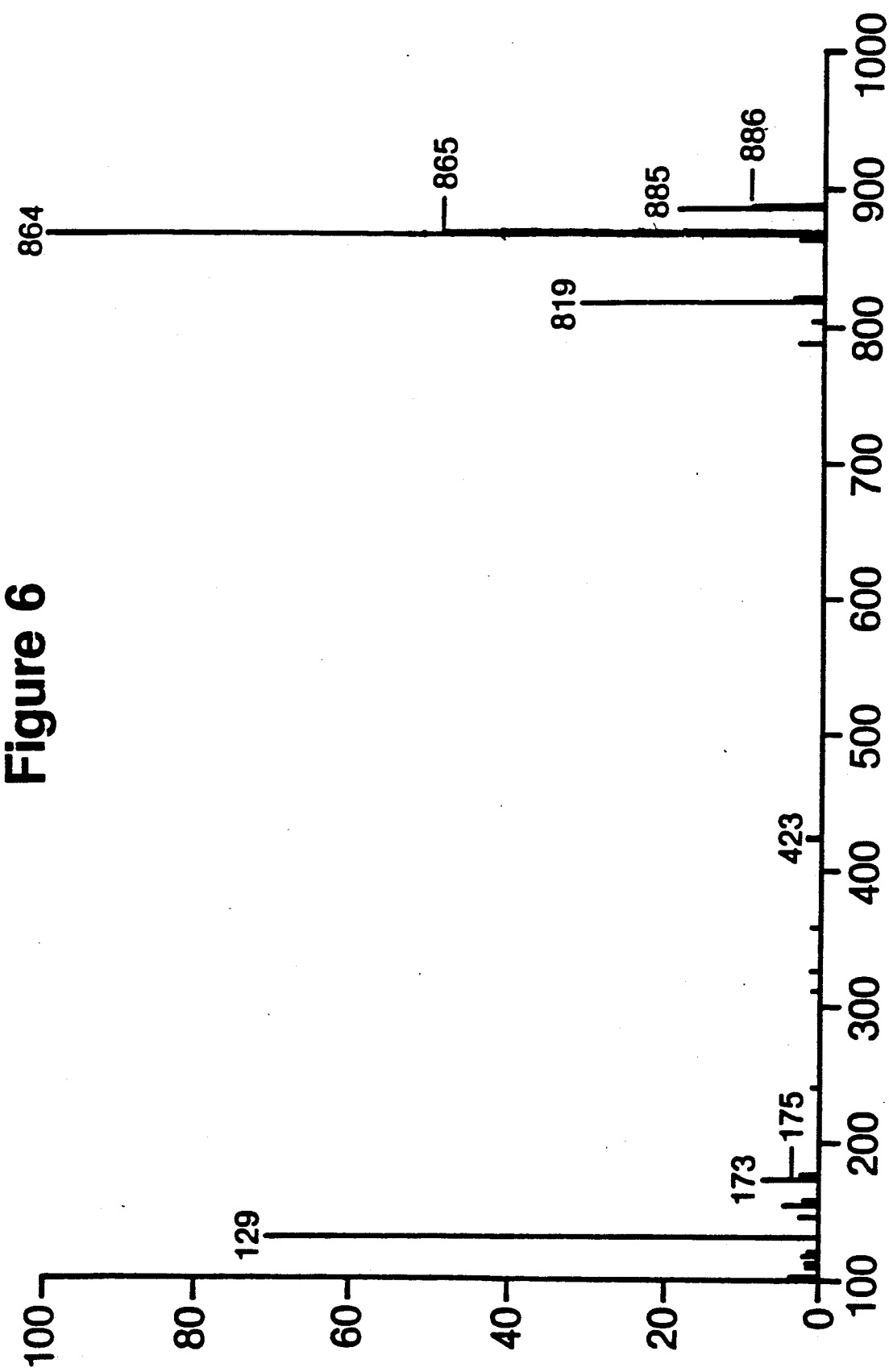
FIG. 6 shows the FD spectrum of A82810 sodium salt.

IR in CHCl$_3$, shown in FIG. 5, shows absorption maxima at the following frequencies (cm$^{-1}$): 2969, 2935, 2879, 2830, 1727, 1589, 1570, 1517, 1489, 1460, 1399, 1379, 1363, 1344, 1316, 1306, 1287, 1265, 1247, 1238, 1216, 1211, 1192, 1163, 1146, 1116, 1102, 1093, 1075, 1068, 1054, 1025, 1009, 1000, 990, 979, 943, 923 and 861.

EXAMPLES 13-22

The following A82810 urethane derivatives can be prepared using the method of Example 12:
A82810 4-chlorophenylurethane
A82810 4-nitrophenylurethane
A828 phenylurethane
A828 4-methylphenylurethane
A82810 4-iodophenylurethane
A82810 4-fluorophenylurethane
A82810 cyclohexylurethane
A82810 2-phenethylurethane
A82810 2-(phenyl)Cyclopropylurethane
A82810 4-phenoxyphenylurethane

EXAMPLE 23

Preparation of A82810 Methyl Ether Derivative

A82810 in the acid form is dissolved in methanol; water (½ volume) is added. The solution is allowed to stand until the ether derivative is formed. The solution is evaporated under vacuum. The product is chromatographed using, for example, silica gel to give to A82810 methyl ether derivative.

EXAMPLES 24 to 26

Using a procedure like that of Example 23 and the appropriate alcohol or thiol, the following A82810 ether derivatives can be prepared:
A82810 n-Propyl Ether Derivative
A82810 Methyl Thioether Derivative
A82810 n-Butyl Ether Derivative

EXAMPLE 27

Chromatographic Identification of A82810

I. TLC
   Adsorbent: silica gel
   System: acetonitrile:acetone (1:1)
   Detection: *Bacillus subtilis*
   $R_f$=0.25
   (In this system A80190 has an $R_f$ of about 0.44, detecting with vanillin spray)
II. HPLC
   Adsorbent: Waters μBondapak C18 (4— ×300-mm column)
   Solvent system: CH$_3$CN:H$_2$O (9:1) containing 1% HOAc
   Detection: refractometer
   Retention time: 5.37 min a
   $^a$For comparison, in this system A80190 has a retention time of approximately b 4.65 minutes.

EXAMPLE 28

Anticoccidial Activity of Synergistic Compositions

Newly hatched chickens are raised in a coccidial-free environment for a seven-day period. On the morning of the eighth day, the chickens are weighed and assigned to treatment groups.

Each group of chicks (usually 4 or 5 chicks per group) is housed in a battery cage during the experiment. A constant lighting schedule and ad libitum access to feed (each experiment contains non-medicated and drug-medicated treatments) and water are provided for the chicks in each battery. Two days after the experiment is initiated, chicks that are designated to be infected are crop-incubated with a pure suspension of coccidial cocysts. The cocyst dosage used in each test is designed to produce clinical coccidiosis in infected nonmedicated animals.

After an additional seven-day growth period, the experiment is terminated. Each group of chicks is weighed, and the amount of feed consumed by each group is determined From these measurements, final bird weights and efficiency of feed utilization are calculated. All birds are then sacrificed, and the intestine and cecum are examined for the presence of coccidial-induced lesions.

Some tests include determination of cocyst production. In this evaluation, fecal material produced by each group of birds is collected during the period when cocyst shedding occurs. The feces are then diluted, and cocysts are counted using a hemacytometer. The measurement is used as an indicator of the reproductive capacity of the parasites in the chicken, and thus, provides an accurate measurement of the ability of a drug to control infections in the animals.

Tables VI to XXIV summarize the results observed when illustrative synergistic compositions of this invention were tested in this manner.

TABLE VI

Anticoccidial Activity Of A82810 Alone And In Combination Against *Eimeria acervulina* Strain 59 And *E. tenella* Strain 155[1]

| Benzeneamine (ppm)[2] | 0 | 0.5 | 1.0 | 1.5 | 2.0 |
|---|---|---|---|---|---|
| | TOTAL LESION SCORE | | | | |
| | 82810 (ppm) | | | | |
| 0 | 10.1 | 12.1 | 10.7 | 8.4 | 5.4 |
| 4 | 12.4 | 7.6 | 6.3 | 4.0 | 3.5 |
| 8 | 10.9 | 6.8 | 3.7 | 3.6 | 2.5 |
| 12 | 10.4 | 5.2 | 4.9 | 2.1 | 4.3 |
| 16 | 10.8 | 6.5 | 3.6 | 1.0 | 0.5 |
| | WEIGHT GAIN, PERCENT OF CONTROL | | | | |
| | A82810 (ppm) | | | | |
| 0 | 67 | 60 | 81 | 85 | 92 |
| 4 | 75 | 81 | 98 | 96 | 97 |
| 8 | 68 | 84 | 89 | 101 | 101 |
| 12 | 73 | 93 | 93 | 92 | 91 |
| 16 | 76 | 86 | 97 | 94 | 97 |

[1]Ionophore-sensitive strains of coccidia
[2]2,4-Dinitro-N-[4-(1,1,2,2-tetrafluoroethoxy)phenyl]-6-(trifluoromethyl)benzeneamine

TABLE VII

Anticoccidial Activity Of A82810 Alone And In Combination Against *Eimeria acervulina* Strain FS-316 And *E. tenella* Strain FS-456[1]

| Benzeneamine (ppm)[2] | 0 | 0.5 | 1.0 | 1.5 | 2.0 |
|---|---|---|---|---|---|
| | TOTAL LESION SCORE | | | | |
| | A82810 (ppm) | | | | |
| 0 | 9.7 | 8.7 | 9.3 | 7.7 | 9.6 |
| 4 | 9.6 | 8.3 | 7.2 | 6.5 | 4.3 |
| 8 | 7.9 | 5.9 | 7.5 | 3.6 | 3.3 |
| 12 | 6.5 | 3.6 | 3.5 | 2.0 | 2.0 |
| 16 | 4.2 | 2.9 | 1.6 | 1.5 | 1.1 |

TABLE VII-continued

Anticoccidial Activity Of A82810 Alone And In Combination Against *Eimeria acervulina* Strain FS-316 And *E. tenella* Strain FS-456[1]

| Benzeneamine (ppm)[2] | 0 | 0.5 | 1.0 | 1.5 | 2.0 |
|---|---|---|---|---|---|
| | WEIGHT GAIN, PERCENT OF CONTROL | | | | |
| | | | A82810 (ppm) | | |
| 0 | 89 | 87 | 89 | 95 | 93 |
| 4 | 90 | 89 | 89 | 93 | 98 |
| 8 | 94 | 87 | 94 | 95 | 98 |
| 12 | 88 | 96 | 95 | 90 | 95 |
| 16 | 87 | 94 | 94 | 90 | 93 |

[1] Ionophore-resistant strains of coccidia
[2] 2,4-Dinitro-N-[4-(1,1,2,2-tetrafluoroethoxy)phenyl]-6-(trifluoromethyl)benzeneamine

TABLE VIII

Anticoccidial Activity of A82810 Alone And Combination Against *E. acervulina* Strain FS-316 And *E. tenella* Strain FS-456[1]

| Compound (ppm)[2] | 0 | 2.5 | 3.0 | 3.5 | 4.0 |
|---|---|---|---|---|---|
| | WEIGHT GAIN, PERCENT OF CONTROL | | | | |
| | | | A82810 (ppm) | | |
| 0 | 80 | 81 | 77 | 85 | 80 |
| 8 | 76 | 88 | 86 | 83 | 89 |
| 10 | 77 | 86 | 88 | 91 | 92 |
| 12 | 75 | 89 | 88 | 91 | 91 |
| 14 | 70 | 88 | 88 | 87 | 90 |
| | AVERAGE INTESTINAL LESION SCORES | | | | |
| | | | A82810 (ppm) | | |
| 0 | 8.1 | 2.3 | 3.3 | 3.0 | 1.2 |
| 8 | 5.9 | 2.9 | 1.1 | 1.3 | 1.2 |
| 10 | 4.8 | 1.7 | 1.4 | 0.7 | 2.6 |
| 12 | 5.9 | 2.0 | 1.1 | 0.4 | 0.5 |
| 14 | 4.5 | 1.5 | 1.3 | 2.0 | 1.4 |
| | AVERAGE CECAL LESION SCORES | | | | |
| | | | A82810 (ppm) | | |
| 0 | 3.3 | 3.2 | 2.9 | 3.2 | 3.0 |
| 8 | 3.3 | 3.1 | 3.4 | 3.3 | 3.1 |
| 10 | 3.2 | 3.3 | 2.8 | 2.6 | 3.0 |
| 12 | 3.1 | 3.3 | 2.9 | 2.7 | 2.8 |
| 14 | 2.8 | 3.1 | 2.8 | 3.6 | 2.0 |

[1] Ionophore-resistant strains of coccidia
[2] 2,4-Dinitro-N-[4-(1,1,2,2-tetrafluoroethoxy)phenyl]-6-(trifluoromethyl)benzeneamine

TABLE IX

Anticoccidial Activity of A82810 Alone And In Combination Against *E. acervulina* Strain FS-316 And *E. tenella* Strain FS-456[1]

| Compound (ppm)[2] | 0 | 4 | 5 | 6 |
|---|---|---|---|---|
| | WEIGHT GAIN, PERCENT OF CONTROL | | | |
| | | A82810 (ppm) | | |
| 0 | 89 | 87 | 95 | 98 |
| 16 | 91 | 89 | 89 | 86 |
| 18 | 91 | 90 | 89 | 87 |
| 20 | 84 | 91 | 86 | 87 |
| 22 | 88 | 89 | 84 | 85 |
| 24 | 85 | 92 | 85 | 84 |
| | AVERAGE INTESTINAL LESION SCORES | | | |
| | | A82810 (ppm) | | |
| 0 | 5.3 | 2.8 | 1.3 | 1.7 |
| 16 | 2.3 | 0 | 0 | 0 |
| 18 | 1.1 | 0 | 0 | 0 |
| 20 | 1.8 | 0 | 0 | 0 |
| 22 | 3.0 | 0 | 0 | 0 |
| 24 | 0.8 | 0 | 0 | 0 |
| | AVERAGE CECAL LESION SCORES | | | |
| | | A82810 (ppm) | | |
| 0 | 3.2 | 3.2 | 2.3 | 3.2 |
| 16 | 2.9 | 1.0 | 0.8 | 0.6 |

TABLE IX-continued

Anticoccidial Activity of A82810 Alone And In Combination Against *E. acervulina* Strain FS-316 And *E. tenella* Strain FS-456[1]

| Compound (ppm)[2] | 0 | 4 | 5 | 6 |
|---|---|---|---|---|
| 18 | 3.0 | 0.4 | 0.5 | 0.5 |
| 20 | 2.9 | 1.2 | 0.8 | 0.6 |
| 22 | 2.6 | 1.2 | 0.4 | 0.5 |
| 24 | 1.6 | 0.8 | 1.6 | 0.3 |

[1] Ionophore-resistant strains of coccidia
[2] 2,4-Dinitro-N-[4-(1,1,2,2-tetrafluoroethoxy)phenyl]-6-(trifluoromethyl)benzeneamine

TABLE X

Anticoccidial Activity of A82810 Alone and In Combination Against *E. acervulina* Strain FS-316

| Compound (ppm)[2] | 0 | 0.5 | 1.0 | 1.5 | 2.0 |
|---|---|---|---|---|---|
| | WEIGHT GAIN, PERCENT OF CONTROL | | | | |
| | | | A82810 (ppm) | | |
| 0 | 69 | 72 | 73 | 73 | 76 |
| 4 | 74 | 75 | 71 | 76 | 83 |
| 8 | 71 | 81 | 80 | 81 | 79 |
| 12 | 82 | 83 | 87 | 84 | 87 |
| 16 | 75 | 87 | 82 | 84 | 90 |
| | AVERAGE INTESTINAL LESION SCORES | | | | |
| | | | A82810 (ppm) | | |
| 0 | 8.5 | 7.3 | 7.8 | 7.9 | 8.8 |
| 4 | 6.9 | 7.1 | 8.4 | 7.5 | 6.5 |
| 8 | 8.4 | 6.4 | 7.3 | 5.9 | 4.3 |
| 12 | 6.3 | 5.3 | 4.8 | 2.4 | 0.3 |
| 16 | 5.8 | 0.1 | 0.9 | 0.1 | 0.1 |

[1] Ionophore-resistant strain of coccidia
[2] 2,4-Dinitro-N-[4-(1,1,2,2-tetrafluoroethoxy)phenyl]-6-(trifluoromethyl)benzeneamine

TABLE XI

Anticoccidial Activity of A82810 Alone And In Combination Against *Eimeria maxima* Strain FS-177[1]

| Compound (ppm)[2] | 0 | 1.5 | 2.0 |
|---|---|---|---|
| | INTESTINAL LESION SCORE | | |
| | | A82810 (ppm) | |
| 0 | 4.0 | 3.7 | 3.6 |
| 8 | 3.6 | 0.4 | 2.5 |
| 12 | 3.9 | 1.3 | 0.8 |
| 16 | 3.3 | 0 | 1.1 |
| | WEIGHT GAIN, PERCENT OF CONTROL | | |
| | | A82810 (ppm) | |
| 0 | 69 | 79 | 92 |
| 8 | 77 | 91 | 88 |
| 12 | 84 | 88 | 86 |
| 16 | 87 | 94 | 87 |

[1] Ionophore-sensitive strain of coccidia
[2] 2,4-Dinitro-N-[4-(1,1,2,2-tetrafluoroethoxy)phenyl]-6-(trifluoromethyl)benzeneamine

TABLE XII

Anticoccidial Activity of A82810 Alone and In Combination Against *Eimeria maxima* Strain FS-177[1]

| Compound (ppm)[2] | 0 | 2 | 6 | 10 |
|---|---|---|---|---|
| | AVERAGE INTESTINAL LESION SCORES | | | |
| | | A82810 (ppm) | | |
| 0 | 3.4 | 1.9 | 0.6 | 0.2 |
| 8 | 2.6 | | | |
| 12 | 2.2 | 0.1 | 0.3 | 0.5 |
| 16 | 2.3 | 0.1 | 0.3 | 0.1 |
| | WEIGHT GAIN, PERCENT OF CONTROL | | | |

TABLE XII-continued

Anticoccidial Activity of A82810 Alone and In Combination Against *Eimeria maxima* Strain FS-177[1]

| Compound (ppm)[2] | 0 | 2 | 6 | 10 |
|---|---|---|---|---|
| | | A82810 (ppm) | | |
| 0 | 105 | 107 | 108 | 102 |
| 8 | 79 | | | |
| 12 | 88 | 111 | 105 | 101 |
| 16 | 102 | 114 | 107 | 91 |

[1]Ionophore-sensitive strain of coccidia
[2]2,4-Dinitro-N-[4-(1,1,2,2-tetrafluoroethoxy)phenyl]-6-(trifluoromethyl)benzeneamine

TABLE XIII

Anticoccidial Activity of A82810 Alone And In Combination Against *E. maxima* Strain LIT-626[1]

| Compound (ppm)[2] | 0 | 1.25 | 1.5 | 1.75 | 2.0 |
|---|---|---|---|---|---|
| | WEIGHT GAIN, PERCENT OF CONTROL | | | | |
| | | A82810 (ppm) | | | |
| 0 | 98 | 99 | 102 | 101 | 94 |
| 8 | 94 | 97 | 94 | 99 | 95 |
| 10 | 99 | 95 | 92 | 97 | 97 |
| 12 | 93 | 94 | 89 | 97 | 95 |
| 14 | 98 | 95 | 93 | 92 | 94 |
| | AVERAGE INTESTINAL LESION SCORES | | | | |
| | | A82810 (ppm) | | | |
| 0 | 4.0 | 3.7 | 3.3 | 4.0 | 3.3 |
| 8 | 2.5 | 1.5 | 3.7 | 0.3 | 2.0 |
| 10 | 3.5 | 0.9 | 1.0 | 3.4 | 1.2 |
| 12 | 1.8 | 2.9 | 1.8 | 2.1 | 0.8 |
| 14 | 3.8 | 1.2 | 1.7 | 2.2 | 1.3 |

[1]Ionophore-resistant strain of coccidia
[2]2,4-Dinitro-N-[4-(1,1,2,2-tetrafluoroethoxy)phenyl]-6-(trifluoromethyl)benzeneamine

TABLE XIV

Anticoccidial Activity of A82810 Alone And In Combination Against *E. maxima* Strain FS-410[1]

| Compound (ppm)[2] | 0 | 2.5 | 3.0 | 3.5 | 4.0 |
|---|---|---|---|---|---|
| | WEIGHT GAIN, PERCENT OF CONTROL | | | | |
| | | A82810 (ppm) | | | |
| 0 | 86 | 90 | 88 | 88 | 91 |
| 8 | 90 | 90 | 92 | 92 | 86 |
| 10 | 90 | 93 | 94 | 87 | 87 |
| 12 | 88 | 91 | 96 | 90 | 98 |
| 14 | 92 | 92 | 89 | 90 | 91 |
| | AVERAGE INTESTINAL LESION SCORES | | | | |
| | | A82810 (ppm) | | | |
| 0 | 3.8 | 3.8 | 3.1 | 3.5 | 2.2 |
| 8 | 3.8 | 2.8 | 1.3 | 2.8 | 1.7 |
| 10 | 3.8 | 2.7 | 1.4 | 3.2 | 1.0 |
| 12 | 3.7 | 0.8 | 0.7 | 0.3 | 1.1 |
| 14 | 3.3 | 1.4 | 1.2 | 0 | 0 |

[1]Ionophore-resistant strain of coccidia
[2]2,4-Dinitro-N-[4-(1,1,2,2-tetrafluoroethoxy)phenyl]-6-(trifluoromethyl)benzeneamine

TABLE XV

Anticoccidial Activity of A82810 Alone And In Combination Against *E. maxima* Strain FS-410

| Compound (ppm)[2] | 0 | 1.25 | 1.5 | 1.75 |
|---|---|---|---|---|
| | WEIGHT GAIN, PERCENT OF CONTROL | | | |
| | | A82810 (ppm) | | |
| 0 | 93 | 93 | 82 | 91 |
| 9 | 90 | 95 | 98 | 94 |
| 10 | 94 | 92 | 98 | 89 |
| 11 | 87 | 96 | 94 | 95 |
| 12 | 84 | 91 | 91 | 92 |
| | AVERAGE INTESTINAL LESION SCORES | | | |
| | | A82810 (ppm) | | |
| 0 | 4.0 | 4.0 | 3.3 | 3.8 |
| 9 | 4.0 | 2.4 | 3.8 | 3.6 |
| 10 | 3.8 | 2.2 | 2.3 | 2.8 |
| 11 | 3.7 | 1.6 | 2.5 | 2.6 |
| 12 | 4.0 | 3.1 | 3.0 | 2.3 |

[1]Ionophore-resistant strain of coccidia
[2]2,4-Dinitro-N-[4-(1,1,2,2-tetrafluoroethoxy)phenyl]-6-(trifluoromethyl)benzeneamine

TABLE XVI

Anticoccidial Activity of A82810 Alone And In Combination Against *E. maxima* Strain FS-410

| Compound (ppm)[2] | 0 | 4 | 5 | 6 |
|---|---|---|---|---|
| | WEIGHT GAIN, PERCENT OF CONTROL | | | |
| | | A82810 (ppm) | | |
| 0 | 65 | 74 | 74 | 81 |
| 16 | 71 | 93 | 88 | 88 |
| 18 | 76 | 90 | 82 | 89 |
| 20 | 81 | 90 | 83 | 90 |
| 22 | 79 | 89 | 87 | 87 |
| 24 | 83 | 86 | 80 | 82 |
| | AVERAGE INTESTINAL LESION SCORES | | | |
| | | A82810 (ppm) | | |
| 0 | 3.3 | 4.0 | 4.0 | 4.0 |
| 16 | 4.0 | 0.5 | 0 | 0.7 |
| 18 | 3.1 | 0 | 0 | 0.2 |
| 20 | 3.4 | 0.5 | 0 | 0 |
| 22 | 3.7 | 0 | 0 | 0.2 |
| 24 | 2.6 | 0 | 0.3 | 0 |

[1]Ionophore-resistant strain of coccidia
[2]2,4-Dinitro-N-[4-(1,1,2,2-tetrafluoroethoxy)phenyl]-6-(trifluoromethyl)benzeneamine

TABLE XVII

Anticoccidial Activity of A82810 Alone And In Combination Against *Eimeria maxima* Strain FS-410[1]

| Compound (ppm)[2] | 0 | 2 | 6 | 10 |
|---|---|---|---|---|
| | LESION SCORE | | | |
| | | A82810 (ppm) | | |
| 0 | 3.9 | 2.3 | 2.7 | 2.4 |
| 8 | 3.3 | | | |
| 12 | 2.9 | 2.1 | 1.4 | 1.1 |
| 16 | 2.4 | 1.9 | 1.1 | 0.8 |
| | WEIGHT GAIN, PERCENT OF CONTROL | | | |
| | | A82810 (ppm) | | |
| 0 | 65 | 85 | 89 | 88 |
| 8 | 68 | | | |
| 12 | 59 | 90 | 88 | 85 |
| 16 | 74 | 90 | 79 | 83 |
| | PERCENT REDUCTION IN OOCYST PRODUCTION | | | |
| | | A82810 (ppm) | | |
| 0 | 0 | 18 | 18 | 36 |
| 8 | 4 | | | |
| 12 | 0 | 12 | 39 | 59 |
| 16 | 0 | 35 | 73 | 78 |

[1]Ionophore-resistant strain of coccidia
[2]2,4-Dinitro-N-[4-(1,1,2,2-tetrafluoroethoxy)phenyl]-6-(trifluoromethyl)benzeneamine

TABLE XVIII

Anticoccidial Activity of A82810 Alone And In Combination Against *Eimeria maxima* Strain FS-410[1]

| Compound (ppm)[2] | 0 | 1.5 | 2.0 |
|---|---|---|---|
| | INTESTINAL LESION SCORE A82810 (ppm) | | |
| 0 | 4.0 | 4.0 | 4.0 |
| 8 | 4.0 | 1.5 | 2.3 |
| 12 | 3.9 | 2.3 | 0.9 |
| 16 | 3.3 | 0.6 | 1.1 |
| | WEIGHT GAIN, PERCENT OF CONTROL A82810 (ppm) | | |
| 0 | 89 | 87 | 89 |
| 8 | 91 | 95 | 100 |
| 12 | 95 | 96 | 99 |
| 16 | 93 | 92 | 96 |

[1] Ionophore-resistant strain of coccidia
[2] 2,4-Dinitro-N-[4-(1,1,2,2-tetrafluoroethoxy)phenyl]-6-(trifluoromethyl)benzeneamine

TABLE XIX

Anticoccidial Activity of A82810 Alone and In Combination Against *Eimeria acervulina* H & C and *Eimeria tenella* Wis[1]

| Compound (ppm)[2] | 0 | 2 | 6 | 10 |
|---|---|---|---|---|
| | AVERAGE INTESTINAL LESION SCORES A82810 (ppm) | | | |
| 0 | 6.2 | 1.2 | 0.4 | 0.3 |
| 8 | 6.0 | | | |
| 12 | 5.1 | 1.0 | 0 | 0.4 |
| 16 | 4.7 | 0.4 | 0.5 | 0.1 |
| | WEIGHT GAIN, PERCENT OF CONTROL A82810 (ppm) | | | |
| 0 | 65 | 98 | 91 | 80 |
| 8 | 62 | | | |
| 12 | 64 | 95 | 90 | 76 |
| 16 | 69 | 97 | 90 | 65 |

[1] Ionophore-sensitive strains of coccidia
[2] 2,4-Dinitro-N-[4-(1,1,2,2-tetrafluoroethoxy)phenyl]-6-(trifluoromethyl)benzeneamine

TABLE XX

Anticoccidial Activity of A82810 Alone And In Combination Against *Eimeria acervulina* Strain FS-273 and *E. tenella* Strain FS-456[1]

| Compound (ppm)[2] | 0 | 2 | 6 | 10 |
|---|---|---|---|---|
| | LESION SCORE A82810 (ppm) | | | |
| 0 | 8.9 | 7.2 | 3.7 | 2.0 |
| 8 | 9.4 | | | |
| 12 | 8.4 | 4.9 | 1.2 | 1.2 |
| 16 | 8.0 | 1.6 | 2.0 | 0.9 |
| | WEIGHT GAIN, PERCENT OF CONTROL A82810 (ppm) | | | |
| 0 | 63 | 68 | 89 | 86 |
| 8 | 70 | | | |
| 12 | 72 | 86 | 92 | 82 |
| 16 | 74 | 95 | 89 | 83 |
| | PERCENT REDUCTION IN OOCYST PRODUCTION A82810 (ppm) | | | |
| 0 | 0 | 22 | 65 | 83 |
| 8 | 17 | | | |
| 12 | 18 | 84 | 94 | 100 |
| 16 | 20 | 95 | 99 | 99 |

[1] Ionophore-resistant strains of coccidia
[2] 2,4-Dinitro-N-[4-(1,1,2,2-tetrafluoroethoxy)phenyl]-6-(trifluoromethyl)benzeneamine

TABLE XXI

Effect of A82810 Alone And In Combination on Growth of Uninfected Chicks

WEIGHT GAIN, PERCENT OF CONTROL A82810 (ppm)

| Compound (ppm)[2] | 0 | 1.25 | 1.5 | 1.75 | 2.0 |
|---|---|---|---|---|---|
| 0 | — | 98 | 101 | 105 | 99 |
| 8 | 100 | 100 | 103 | 98 | 102 |
| 10 | 101 | 102 | 98 | 97 | 100 |
| 12 | 94 | 98 | 102 | 97 | 97 |
| 14 | 98 | 99 | 99 | 100 | 96 |

TABLE XXII

Anticoccidial Activity of A82810 Alone And In Combination Against *Eimeria acervulina* Strain 59 and *E. tenella* Strain 155[1]

| Compound (ppm)[2] | 0 | 1.5 | 2.0 |
|---|---|---|---|
| | TOTAL LESION SCORE A82810 (ppm) | | |
| 0 | 11.5 | 8.9 | 4.5 |
| 4 | 11.2 | 3.7 | 1.9 |
| 8 | 8.7 | 2.2 | 0.8 |
| 12 | 5.0 | 1.3 | 0.8 |
| 16 | 4.4 | 1.3 | 0.3 |
| | WEIGHT GAIN, PERCENT OF CONTROL A82810 (ppm) | | |
| 0 | 70 | 93 | 97 |
| 4 | 80 | 92 | 105 |
| 8 | 78 | 101 | 98 |
| 12 | 80 | 93 | 92 |
| 16 | 92 | 92 | 102 |

[1] Ionophore-sensitive strains of coccidia
[2] 4-chloro-N-[2,4-dinitro-6-(trifluoromethyl)phenyl]-1-naphthaleneamine

TABLE XXIII

Anticoccidial Activity of A82810 Alone And In Combination Against *Eimeria maxima* Strain FS-177[1]

| Compound (ppm)[2] | 0 | 1.5 | 2.0 |
|---|---|---|---|
| | INTESTINAL LESION SCORE A82810 (ppm) | | |
| 0 | 3.9 | 3.5 | 3.3 |
| 4 | 3.8 | 3.1 | 0.8 |
| 8 | 3.8 | 1.3 | 1.5 |
| 12 | 3.2 | 1.0 | 0.3 |
| 16 | 1.0 | 0.5 | 0.5 |
| | WEIGHT GAIN, PERCENT OF CONTROL A82810 (ppm) | | |
| 0 | 87 | 99 | 100 |
| 4 | 87 | 95 | 98 |
| 8 | 80 | 88 | 97 |
| 12 | 85 | 88 | 93 |
| 16 | 84 | 87 | 86 |

[1] Ionophore-sensitive strain of coccidia
[2] 4-chloro-N-[2,4-dinitro-6-(trifluoromethyl)phenyl]-1-naphthaleneamine

TABLE XXIV

Anticoccidial Activity of A82810 Alone And In Combination Against *E. acervulina* Strain 59 And *E. tenella* Strain 155[1]

| Compound (ppm)[2] | 0 | 1.25 | 1.5 | 1.75 |
|---|---|---|---|---|
| | WEIGHT GAIN, PERCENT OF CONTROL A82810 (ppm) | | | |
| 0 | 70 | 87 | 80 | 82 |
| 4 | 73 | 79 | 84 | 83 |
| 8 | 66 | 94 | 91 | 88 |
| 12 | 72 | 84 | 87 | 85 |
| 16 | 67 | 76 | 79 | 70 |
| | AVERAGE INTESTINAL LESION SCORES A82810 (ppm) | | | |

TABLE XXIV-continued

Anticoccidial Activity of A82810 Alone And
In Combination Against *E. acervulina* Strain 59
And *E. tenella* Strain 155[1]

| Compound (ppm)[2] | 0 | 1.25 | 1.5 | 1.75 |
|---|---|---|---|---|
| 0 | 6.0 | 6.0 | 3.6 | 2.3 |
| 4 | 6.2 | 3.7 | 3.4 | 3.1 |
| 8 | 6.9 | 1.3 | 0.3 | 0.4 |
| 12 | 6.6 | 0.5 | 2.1 | 0.3 |
| 16 | 3.8 | 1.8 | 0 | 0.8 |

AVERAGE CECAL LESION SCORES
A82810 (ppm)

| | | | | |
|---|---|---|---|---|
| 0 | 3.2 | 3.2 | 2.6 | 2.0 |
| 4 | 2.9 | 2.9 | 2.8 | 2.6 |
| 8 | 3.5 | 2.6 | 2.3 | 1.6 |
| 12 | 3.0 | 1.8 | 1.4 | 0.7 |
| 16 | 2.9 | 1.7 | 0.9 | 0.5 |

[1]Ionophore-sensitive strains of coccidia
[2]4-Bromo-N-[2,4-dinitro-6-trifluoromethyl)phenyl]-1-naphthaleneamine

EXAMPLE 29

A82810 Modified Chick Ration for Coccidiosis Control

A balanced, high-energy ration adapted to feed chicks for rapid weight gain is prepared by the following recipe:

| Ingredient | % | lbs |
|---|---|---|
| Ground yellow corn | 50 | 1,000 |
| Soybean meal, solvent-extracted dehulled, finely ground, 50 percent protein | 31.09 | 621.8 |
| Animal fat (beef tallow) | 6.5 | 130 |
| Dried fish meal, with solubles (60% protein) | 5.0 | 100 |
| Distillers' solubles from corn | 4.0 | 80 |
| Dicalcium phosphate, feed grade | 1.8 | 36 |
| Calcium carbonate | 0.8 | 16 |
| Vitamin premix (representing vitamins A, D, E, K, and B$_{12}$, choline, niacin, pantothenic acid, riboflavin, biotin, with glucose bulking agent) | 0.5 | 10 |
| Trace mineral premix (representing MnSO$_4$, ZnO, KI, FeSO$_4$, CaCO$_3$) | 0.2 | 4 |
| 2-Amino-4-hydroxybutyric acid (hydroxy analog of methionine) | 0.1 | 2 |
| A82810 (Na Salt) | 0.01 | 0.2 |

These substances are mixed in accordance with standard feed-mixing techniques. Chicks fed such a ration, with water ad libitum, are protected against exposure to coccidiosis; weight gains are comparable to those of coccidiosis-free chicks fed a similar, unmedicated diet.

EXAMPLES 30-32

A82810-Synergistic Chick Ration Compositions for Coccidiosis Control

Chick ration is prepared as described in Example 29, but using the following A82810 synergistic combinations as the active ingredients:

| Ingredient | ppm |
|---|---|
| A82810 | 0.25-10 |
| 2,4-dinitro-N-[4-(1,1,2,2-tetrafluoroethoxy)phenyl]-6-(trifluoromethyl)benzeneamine | 4-24 |
| A82810 | 0.25-10 |
| 4-chloro-N-[2,4-dinitro-6-(trifluoromethyl)phenyl]-1-naphthaleneamine | 4-24 |
| A82810 | 0.25-10 |
| 4-bromo-N-[2,4-dinitro-6-(trifluoromethyl)phenyl]-1-naphthaleneamine | 4-24 |

EXAMPLE 33

A82810-Improved Beef-Cattle Ration

A balanced high-grain beef-cattle ratin is prepared as follows:

| Ingredient | % | lbs |
|---|---|---|
| Finely ground corn | 67.8 | 1356 |
| Ground corn cob | 10 | 200 |
| Dehydrated alfalfa meal, 17 percent protein | 5 | 100 |
| Dehulled soybean meal, solvent extracted, 50 percent protein | 9.9956 | 199.912 |
| Cane molasses | 5 | 100.0 |
| Urea | 0.6 | 12.0 |
| A82810 (Na salt) | 0.0044 | 0.088 |
| Dicalcium phosphate, feed grade | 0.5 | 10.0 |
| Calcium carbonate | 0.5 | 10.0 |
| Sodium chloride | 0.3 | 6.0 |
| Trace mineral premix | 0.03 | 0.6 |
| Vitamin A and D$_2$ premix* | 0.07 | 1.4 |
| Vitamin E premix** | 0.05 | 1.0 |
| Calcium propionate | 0.15 | 3.0 |

*Containing per pound: 2,000,000 I.U. of vitamin A; 227,200 I.U. of vitamin D$_2$ and 385.7 g of soybean feed with 1% oil added
**Corn distillers dried grains with solubles containing 20,000 I.U. of d-alpha-tocopheryl acetate per pound The mixed feed is compressed into pellets. At an average daily ingestion rate of 15 pounds of feed per animal, this feed supplies approximately 300 mg of A82810 (Na salt) per animal per day.

EXAMPLE 34

A828810-Improved Swine Ration

A balanced swine farrowing ration is prepared as follows:

| Ingredient | % | lbs/ton |
|---|---|---|
| Ground yellow corn | 65.10 | 1302 |
| Soybean oil meal, solvent extracted dehulled | 18.50 | 370 |
| Dried-beet pulp | 10.00 | 200 |
| Dicalcium phosphate | 2.90 | 58 |
| Calcium carbonate | 1.20 | 24 |
| Swine vitamin premix[1] | 1.10 | 22 |
| Salt (NaCl) | 0.55 | 11 |
| Choline chloride, 25% | 0.35 | 7 |
| Trace-mineral premix[2] | 0.15 | 3 |
| Vitamin A premix[3] | 0.10 | 2 |
| Hydroxy analog of Methionine | 0.05 | 1 |

| Ingredient | % | lbs/ton |
|---|---|---|
| Total | 100.00 | 2000 |

[1]Each kg of premix contains the following: 77,161 USP units Vitamin D$_2$; 2,205 I.U. of Vitamin E; 441 mg riboflavin; 1,620 mg pantothenic acid; 2,205 mg niacin; 4.4 mg Vitamin B$_{12}$; 441 mg Vitamin K, 19,180 mg choline; 110 mg folic acid; 165 mg pyridoxine; 110 mg thiamine, 22 mg biotin.

[2]Each kg of premix contains the following: 50 g of manganese as manganese sulfate, 100 g of zinc as zinc carbonate; 50 g of iron as ferrous sulfate, 5 g of copper as copper oxide; 1.5 g of iodine as potassium iodide and 150 g maximum and 130 g minimum calcium as calcium carbonate.

[3]Each kg of premix contains 6,6138,00 USP units Vitamin A.

For 200 pounds of this ration, a premix is prepared by adding A82810 (10 g) to a small amount of solvent-extracted soybean feed, grinding them in a mortar and pestle, and diluting the ground mixture to one pound with additional solvent-extracted soybean feed. This premix is then added to 200 lb. of the above-described swine ration, mixing by standard techniques. This medicated feed provides a level of 100 grams of A82810 per ton of basal ration. Medicated feed is fed to sows for at least one day, and preferably from seven to ten days, prior to farrowing and after farrowing for as long as is desirable.

Larger or smaller quantities of medicated ration with varying levels of A82810 are prepared by varying the quantity of A82810 in the premix and/or the quantity of basal ration.

Sows are fed at rates of from 1.0 to 10 grams of A82810 per 100 pounds of feed. The medicated feed is available ad libitum with water. Usually, sows consume about 6–8 lb of ration per day.

EXAMPLE 35

A82810-Formulation for Piglets

A82810 is dissolved in a small amount of ethanol. This ethanol solution is suspended in polyethylene glycol 200. The suspension is concentrated so that each unit dose has a volume of about 0.5 to 2 mL. Such suspensions are given to young pigs at rates of 0.5 to 50 mg per lb, three times a day by gavage.

EXAMPLE 36

Improved Ration for Control of Swine Dysentery

A premix is prepared by standard methods using the following ingredients:

| Ingredient | Amounts (g/kg) |
|---|---|
| Active Compound | 150.0 |
| Calcium Silicate | 20.0 |
| Calcium Carbonate (Oyster Shell Flour) | 830.0 |
| Total Weight | 1000 g |

This premix is added to commercial swine ration, using standard feed-mixing techniques, to give a final level of about 100 g of active compound/ton of ration.

We claim:

1. A process for producing antibiotic A82810

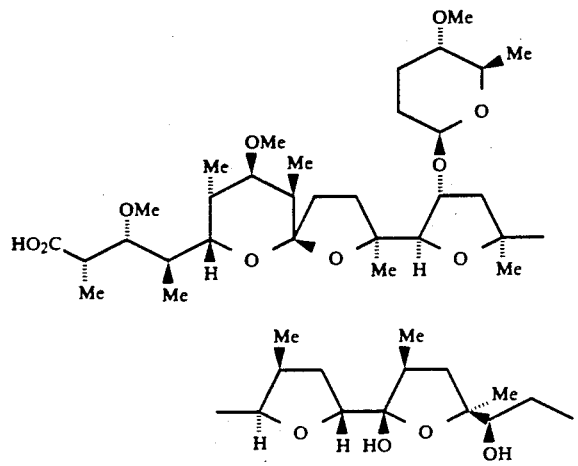

which comprises cultivating *Actinomadura fibrosa* sp. nov. NRRL 18348, or an A82810-producing mutant thereof, in a culture medium containing assimilable sources of carbon, nitrogen, and inorganic salts under submerged aerobic fermentation conditions until antibiotic A82810 is produced.

2. The process of claim 1 which includes the additional step of separating A82810 from the culture medium.

3. The process of claim 1 wherein *Actinomadura fibrosa* sp. nov. NRRL 18348 is used.

4. A biologically purified culture of *Actinomadura fibrosa* sp. nov. NRRL 18348, or an A82810-producing mutant thereof.

5. The culture of claim 4 which is *Actinomadura fibrosa* sp. nov. NRRL 18348.

* * * * *

UNITED STATES PATENT AND TRADEMARK OFFICE
CERTIFICATE OF CORRECTION

PATENT NO. : 5,098,834  Page 1 of 2

DATED : March 24, 1992

INVENTOR(S) : Hamill, et al.

It is certifed that an error appears in the above-identified patent and that said Letters Patent is hereby corrected as shown below:

On the title page, item [54] and column 1, line 1, "A8210" should read --A82810--.

On the title page, item [57], "acyl ester and urethane derivatives" should read --alkyl ether and urethane derivatives--.

Column 1, line 61, "raphy" should read --chromatography--.

Column 4, line 44, "inClude" should read --include--.

Column 6, line 32, "A82810are" should read --A82810.1 are--.

Column 7, line 27, "A82810produced" should read --"A82810.1 produced--; line 42, "A82810produced" should read --A82810.1 produced--; line 46, "A82810did" should read --A82810.1 did--.

Column 9, line 19, "A82810. land" should read --A82810.1 and--.

Column 15, line 59, "Combinations" should read --combinations--; line 60, "anticoceidial" should read --anticoccidial--.

Column 16, line 7, " from about S" should read --from about 5--.

Column 18, line 55, following "circle at", add --250 rpm--.

Column 23, line 19, "A828" should read --A82810--; line 20, "A828" should read --A82810--; line 25, "2-(phenyl) Cyclopropylurethane" should read --2-(phenyl) cyclopropylurethane--.

UNITED STATES PATENT AND TRADEMARK OFFICE
CERTIFICATE OF CORRECTION

PATENT NO.    :    5,098,834

DATED         :    March 24, 1992

INVENTOR(S)   :    Hamill, et al.

It is certifed that an error appears in the above-identified patent and that said Letters Patent is hereby corrected as shown below:

Column 24, line 11, 1st and 2nd occurance, "cocysts" should read --oocysts--; line 22, "cocyst" should read --oocyst--; line 24-25, "cocyst" should read --oocyst--; line 26 "cocysts" should read --oocysts--.

Signed and Sealed this

Second Day of November, 1993

*Attest:*

BRUCE LEHMAN

*Attesting Officer*   *Commissioner of Patents and Trademarks*